(12) United States Patent
Hurley et al.

(10) Patent No.: US 10,556,860 B2
(45) Date of Patent: Feb. 11, 2020

(54) HTERT MODULATORS AND METHODS OF USE

(71) Applicant: Arizona Board of Regents on Behalf of the University of Arizona, Tucson, AZ (US)

(72) Inventors: Laurence Hurley, Tucson, AZ (US); Vijay Gokhale, Tucson, AZ (US); HyunJin Kang, Tucson, AZ (US); Kui Wu, Tucson, AZ (US)

(73) Assignee: ARIZONA BOARD OF REGENTS, Middleton, WI (US)

( * ) Notice: Subject to any disclaimer, the term of this patent is extended or adjusted under 35 U.S.C. 154(b) by 0 days.

(21) Appl. No.: 15/779,132

(22) PCT Filed: Nov. 30, 2016

(86) PCT No.: PCT/US2016/064287
§ 371 (c)(1),
(2) Date: May 25, 2018

(87) PCT Pub. No.: WO2017/095969
PCT Pub. Date: Jun. 8, 2017

(65) Prior Publication Data
US 2018/0346415 A1    Dec. 6, 2018

Related U.S. Application Data

(60) Provisional application No. 62/261,838, filed on Dec. 1, 2015.

(51) Int. Cl.
| | |
|---|---|
| *A61K 31/5377* | (2006.01) |
| *A61K 31/505* | (2006.01) |
| *A61K 31/4995* | (2006.01) |
| *A61K 31/4402* | (2006.01) |
| *A61K 31/17* | (2006.01) |
| *C07C 275/54* | (2006.01) |
| *C07D 401/12* | (2006.01) |
| *C07D 403/04* | (2006.01) |
| *C07D 239/34* | (2006.01) |
| *C07D 239/52* | (2006.01) |
| *C07D 241/18* | (2006.01) |
| *C07D 295/088* | (2006.01) |
| *A61P 35/00* | (2006.01) |
| *C07D 219/08* | (2006.01) |

(52) U.S. Cl.
CPC ........... *C07C 275/54* (2013.01); *A61K 31/17* (2013.01); *A61K 31/4402* (2013.01); *A61K 31/4995* (2013.01); *A61K 31/505* (2013.01); *A61K 31/5377* (2013.01); *A61P 35/00* (2018.01); *C07D 219/08* (2013.01); *C07D 239/34* (2013.01); *C07D 239/52* (2013.01); *C07D 241/18* (2013.01); *C07D 295/088* (2013.01); *C07D 401/12* (2013.01); *C07D 403/04* (2013.01)

(58) Field of Classification Search
None
See application file for complete search history.

(56) References Cited

U.S. PATENT DOCUMENTS

| | | | |
|---|---|---|---|
| 4,552,900 A | * | 11/1985 | Sirrenberg .......... C07D 239/34 514/269 |
| 4,727,077 A | | 2/1988 | Haga et al. |
| 5,102,884 A | | 4/1992 | Haga et al. |
| 5,399,691 A | | 3/1995 | Kon et al. |
| 2004/0005601 A1 | | 1/2004 | Siddiqui-Jain et al. |

FOREIGN PATENT DOCUMENTS

| | | |
|---|---|---|
| EP | 0413977 | 2/1991 |
| EP | 0545411 | 6/1993 |

OTHER PUBLICATIONS

Gurulingappa, Hallur. Synthesis and antitumor evaluation of benzoylphenylurea analogs. Bioorganic & Medicinal Chemistry Letters 14 (2004) 2213-2216.*
International Search Report and Written Opinion, International Patent Application No. PCT/US2016/064287, dated Apr. 5, 2017, 10 pages.
European Search Report, Ep Patent Application No. 16871454.1, dated Jul. 4, 2019, 3 pages.

* cited by examiner

*Primary Examiner* — Samantha L Shterengarts
(74) *Attorney, Agent, or Firm* — Casimir Jones, SC

(57) ABSTRACT

The present invention provides hTERT modulators and methods for producing and using the same. In particular, the present invention provide a compound of the formula as described herein. Some aspects of the invention are based on the characterization of the effect of hTERT core promoter region mutants on the 5-12 G-quadruplex structure and its stability. It is believed that some of the compounds of the invention bind selectively to the G-quadruplex in the hTERT core promoter mutant, which results in reversal of the effect of mutant promoter activation.

11 Claims, 7 Drawing Sheets

HTERT MODULATORS AND METHODS OF USE

CROSS-REFERENCE TO RELATED APPLICATIONS

This application claims the priority benefit of U.S. Provisional Application No. 62/261,838, filed Dec. 1, 2015, which is incorporated herein by reference in its entirety.

STATEMENT REGARDING FEDERALLY FUNDED RESEARCH

This invention was made with government support under Grant Nos. R01CA153821 and R01CA177585 awarded by NIH. The government has certain rights in the invention.

FIELD OF THE INVENTION

The present invention relates to hTERT modulators and methods for producing and using the same.

BACKGROUND OF THE INVENTION

Activation of telomerase is a hallmark of cancer in the early stages of tumorigenesis and is associated with telomere elongation, genetic instability, and subsequent immortalization of cells. There are several strategies for overcoming activated telomerase that are potentially useful for therapeutic treatment, including targeting the telomerase holoenzyme, telomeric G-quadruplexes with small molecules, human telomerase reverse transcriptase (hTERT), and human telomerase RNA, and using immune therapy.

hTERT is a catalytic subunit of telomerase and a critical element for telomerase activity. Expression of hTERT is not usually activated in normal cells, although other components of telomerase are expressed. In addition, hTERT has various telomere-independent functions, including enhancement of cellular proliferation, DNA damage response through change in chromatin structure, and inhibition of apoptosis by upregulation of BCL2 expression. These functions are independent of each other.

Overexpression of hTERT for cell immortalization or telomerase activation occurs in several ways, including increased gene copy number and modulation at the transcription level. At the transcription level, the hTERT promoter does not have TATA or CAAT boxes but does have several transcription factor binding sites within 1 Kb of the transcription start site and is controlled by epigenetic changes, such as chromatin remodeling or methylation of the CpG islands in the promoter region. With this transcription machinery, 0.004 RNA molecules per cell in telomerase-negative cells are elevated to 0.2-6 RNA molecules per cell in telomerase-positive tumor-derived cells, showing a strong correlation between telomerase activity and hTERT transcription level.

The essential region for activation of transcription is at the core promoter region, −181 base pairs from the transcription start site. This region includes the E-box for MYC and other elements for transcription activation. An additional upstream region likely contains transcription-repressing elements, because the longer promoter region shows decreased promoter activity. This core promoter region becomes nuclease sensitive during cell proliferation. Because the hTERT core promoter is selectively activated in cancer cells, it is targeted for gene therapy by utilizing the promoter for expression of cytotoxic tumor-suppressing proteins.

The present inventors have previously shown, by various biochemical experiments including DMS footprinting experiments, that end-to-end stacked G-quadruplex structures are formed in the core promoter element from 12 G-tracts. One of these structures has a unique 3:26:1 loop configuration; the 26-base internal loop is a hairpin structure and responsible for the unique cooperative folding of this G-quadruplex, which is believed to be important in transcription silencing. Stabilization of this G-quadruplex structure using small molecules causes repression of hTERT promoter activity. Significantly the mouse TERT lacks these 12 G-tracts and has a 16-fold higher transcriptional activation level.

Several groups have recently demonstrated that many different kinds of tumors have somatic mutations within the hTERT promoter region at positions −124, −124/125, −138/139, and −146 from the ATG start site. A G-to-A mutation (G/A) in the antisense strand is proposed to generate an ETS/TCF element that would increase binding of the ETS transcription factor for activation of hTERT transcription. Significantly, these mutations are also localized in the G-quadruplex with the 3:26:1 loop configuration. While it has been demonstrated in a number of oncogene promoters that the G-quadruplex functions as a silencer element, it has also been shown recently that, in the case of BCL2, the i-motif can act as a transcription activator, validating both secondary DNA structures as transcriptional targets for modulation of gene expression. Therefore, it can be reasonably inferred that DNA structural changes to either a G-quadruplex or an i-motif as a result of these mutations would also affect the transcription activity of the mutated hTERT promoter as well as the binding of the ETS transcription factor to the duplex form. Accordingly, modulation of transcription activity of the mutated hTERT promoter can be used to treat cancer as well as other clinical conditions associated with a transcription-activating mutation in an hTERT core promoter region or hTERT overexpression due to genomic rearrangements such as translocation or amplification.

Therefore, there is a need for a compound that can modulate transcription activity of hTERT to treat cancer and other clinical conditions associated with transcription or overexpression of hTERT.

BRIEF DISCUSSION OF THE DRAWINGS

FIGS. 7A and 7B are a set of graphs showing (A) effects of compounds (0.25 µM) on hTERT expression in MCF7 cells after 48 hours and (B) effects of compounds (0.125 µM) on hTERT expression in U87 cells after 48 hours.

Figure 8:
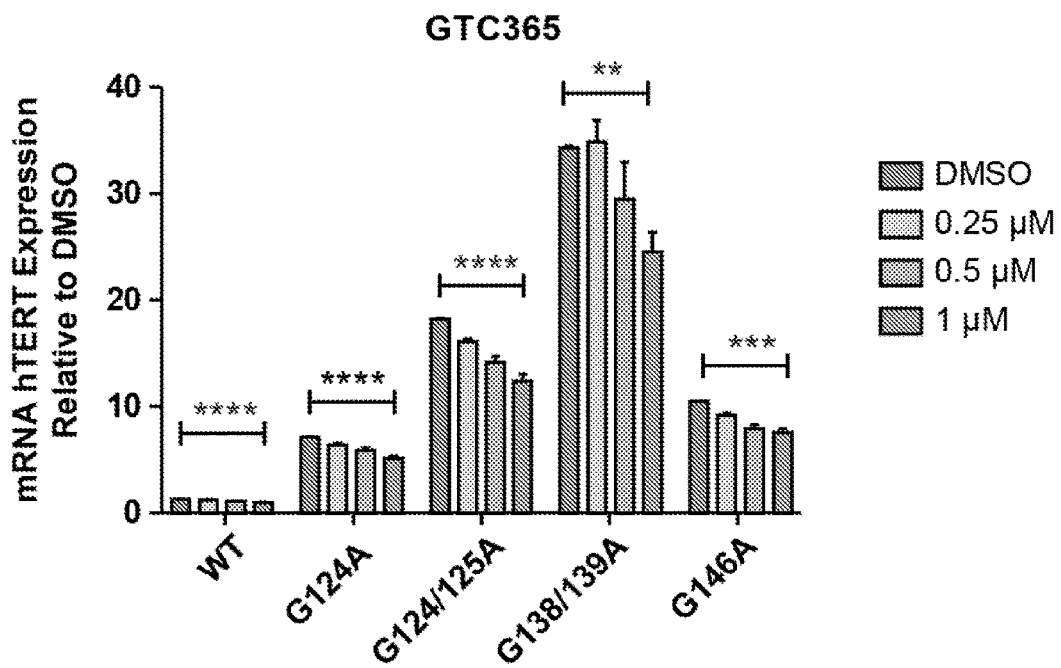

FIG. 8 is a graph showing dose-dependent effect of GTC365 on hTERT mRNA level in melanoma cells carrying WT, G124A, G124/125A, G138/139A and G146A.

Figure 9:
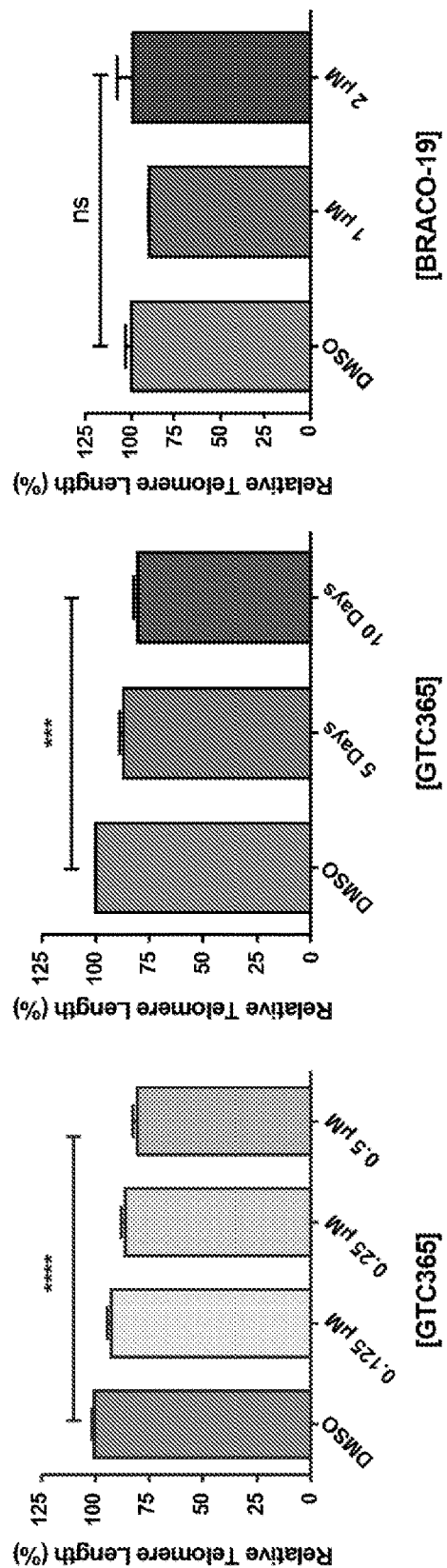

FIG. 9 is a set of graphs showing dose- and time-dependent loss of telomere length following short-term exposure to GTC365 and BRACO-19. MCF7 cells were treated with different doses of GTC365 for 10 days (left), 0.5 µM of GTC365 for 5 or 10 days (center), or different doses of BRACO-19 for 5 days (right).

FIGS. 10A and 10B are a set of graphs showing (A) comparison of kinetics of initial folding rate of the WT 5-12 G-quadruplex with GTC365 and BRACO-19 by the temperature-jump method. (B) Enhanced initial folding rate of the 5-12 G-quadruplexes carrying different hTERT mutants by GTC365. The time-course CD signal of preheated oligo with compound or DMSO in a buffer containing 10 mM Tris-HCl (pH 7.5) and 5 mM KCl was monitored at 262 nm and 25° C.

Figure 11:
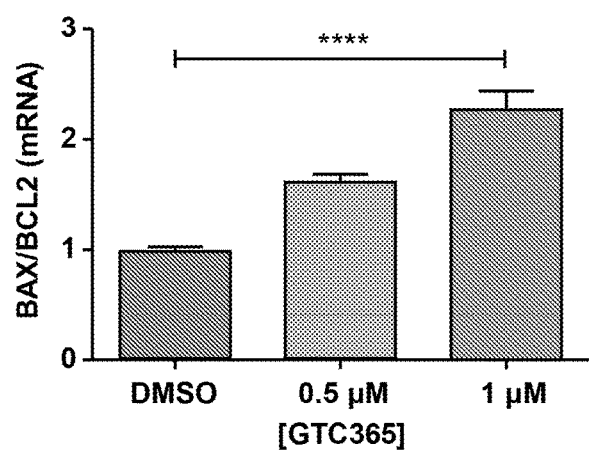

FIG. 11 is a graph showing increase of BAX/BCL2 ratios by GTC365 in mRNA levels. MCF7 cells were treated with GTC365 for 72 h and then subjected to qPCR and immunoblot analysis. The relative ratio of BAX/BCL2 was determined compared with a DMSO-treated sample.

Figure 12:
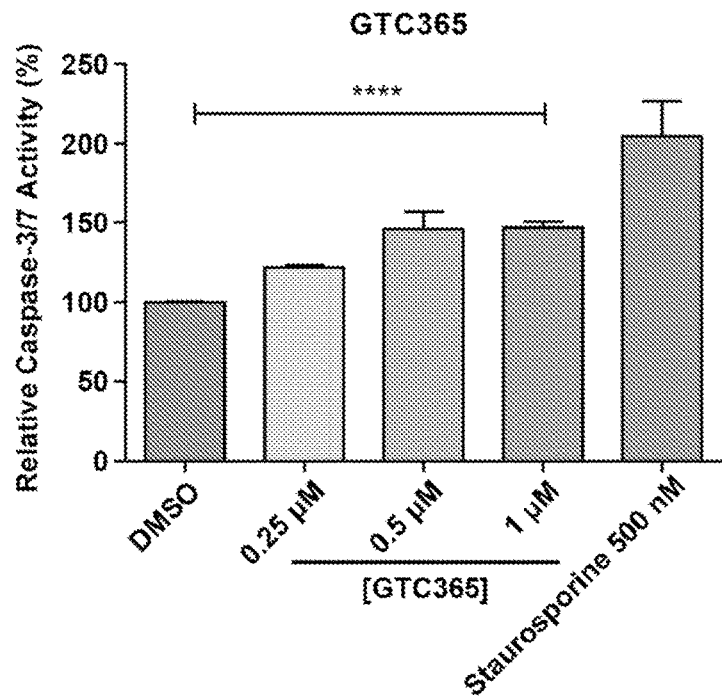

FIG. 12 is a graph showing activation of caspase-3 by GTC365.

Figure 13:
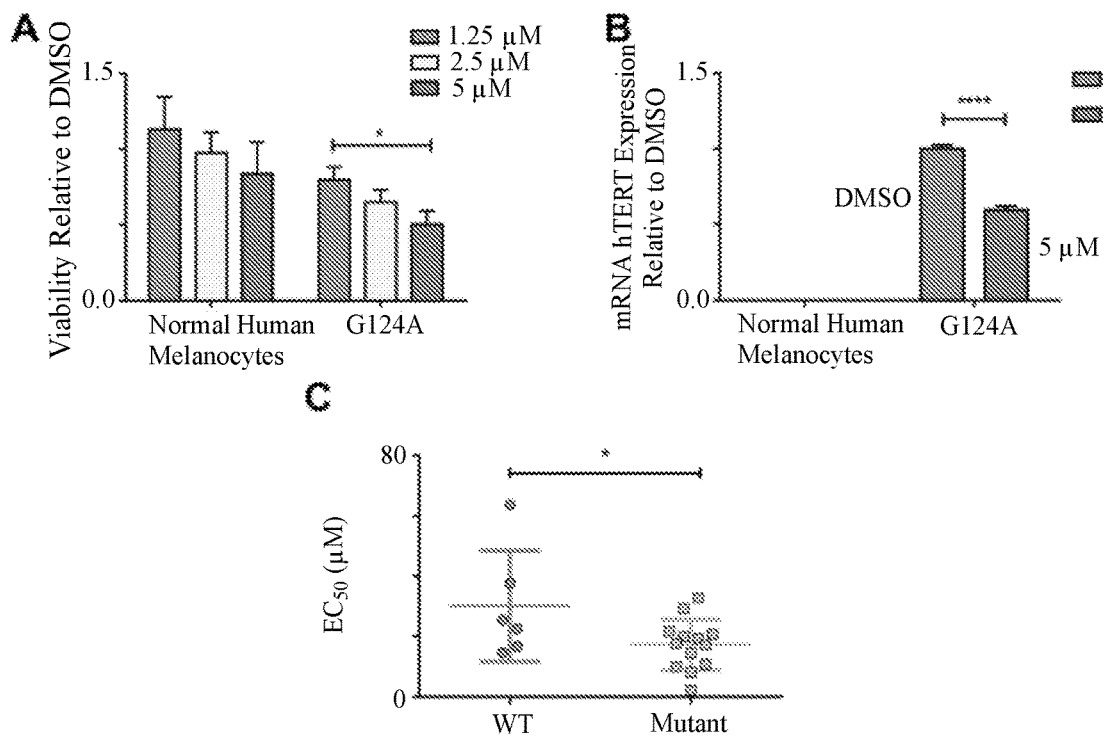

FIGS. 13A-13C are a set of graphs showing selective reduction in viability (A) and hTERT expression (B) in melanoma cells carrying hTERT core promotor mutations. NHM-002 (normal human melanocytes) and a G124A mutant cell line were treated with vehicle, 1.25, 2.5, and 5 µM GTC365 for 72 h. Viability was reduced in hTERT mutant melanoma cells by 50% (left). GTC365 caused minimal reduction in NHM-002 viability and was not statistically significant. hTERT mRNA expression was also reduced in melanoma cells treated with GTC365 for 72 h. hTERT expression was undetectable in NHM-002 cells (right). (C) Differential response to GTC365 in WT and promoter mutant cell lines.

SUMMARY OF THE INVENTION

Some aspects of the invention are based on the characterization of the effect of hTERT core promoter region mutants on the 5-12 G-quadruplex structure and its stability. Other aspects of the invention are based on identification of compounds by the present inventors that modulate hTERT activity. Without being bound by any theory, it is believed that some of the compounds of the invention bind selectively to the G-quadruplex in the hTERT core promoter mutant, which results in reversal of the effect of mutant promoter activation.

In one specific aspect of the invention, a method is provided for treating a patient suffering from a clinical condition associated with a transcription-activating genetic change associated with the hTERT promoter region. As used herein, the term "a transcription-activating genetic change associated with the hTERT promoter region" includes hTERT overexpression due to genomic rearrangements such as translocation or amplification. Methods of the invention include administering to a patient suffering from a clinical condition associated with a transcription-activating genetic change associated with the hTERT core promoter region a therapeutically effective amount of compound I, compound II, or a pharmaceutically acceptable salt thereof, or a prodrug thereof, or a mixture thereof. Compounds I and II are of the formula:

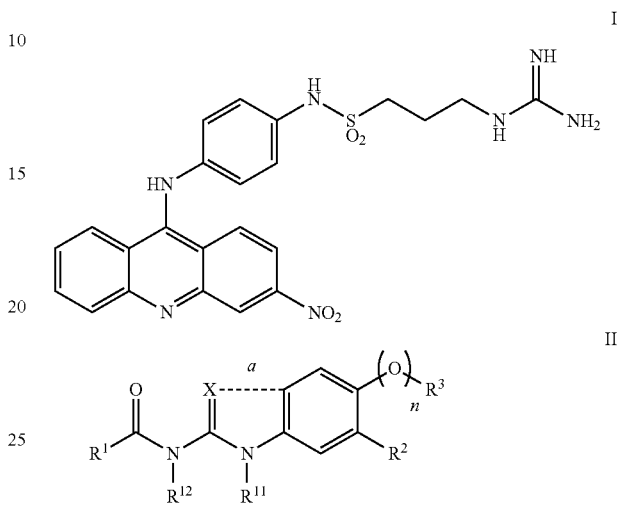

respectively, where X is O or N such that when X is O, bond a is absent and when X is N, bond a is present; n is 0 or 1 such that: when n=0, $R^3$ is —NHC(=NH)NH$_2$; and when n=1, $R^3$ is hydrogen, alkyl, cycloalkyl, optionally substituted heterocycloalkyl, optionally substituted heteroaryl or optionally substituted aryl, wherein each substituent is independently selected from the group consisting of halogen, cyano, nitro, azido, haloalkyl, cycloalkyl, heteroaryl, aryl, —NR$^7$R$^8$, —NR$^7$C(O)R$^8$, —C(O)NR$^7$R$^8$, —C(O)R$^9$, —C(O)OR$^9$, —S(O)R$^9$, —SO$_2$R$^9$, —SO$_2$NR$^7$R$^8$, —OR$^9$ and —SR$^9$; $R^1$ is optionally substituted aryl or optionally substituted heteroaryl, wherein each substituent is independently selected from the group consisting of halogen, cyano, nitro, azido, haloalkyl, cycloalkyl, —NR$^4$R$^5$, —NR$^4$C(O) R$^5$, —C(O)NR$^4$R$^5$, —C(O)R$^6$, —C(O)OR$^6$, —S(O)R$^6$, —SO$_2$R$^6$, —SO$_2$NR$^4$R$^5$, —OR$^6$, and —SR$^6$; $R^2$ is selected from the group consisting of hydrogen, halogen, alkyl, haloalkyl and cycloalkyl; each of $R^4$ and $R^5$ is independently selected from the group consisting of hydrogen, alkyl, alkenyl, alkynyl, heteroaryl, aryl and cycloalkyl, or $R^4$ and $R^5$ together with the nitrogen atom to which they are attached to form an optionally substituted monocyclic or bicyclic ring with one or more heteroatoms; $R^6$ is selected from the group consisting of hydrogen, alkyl, alkenyl, alkynyl, heteraryl, aryl, cycloalkyl, wherein the alkyl, alkenyl, heteraryl, aryl and cycloalkyl are optionally substituted with one or more halo, cyano, alkylamino, alkoxy, aryl, heteroaryl or heterocyclyl groups; each of $R^7$ and $R^8$ is independently selected from the group consisting of hydrogen, alkyl, alkenyl, alkynyl, heteroaryl, aryl and cycloalkyl, or $R^7$ and $R^8$ together with the nitrogen group to which they are attached to form an optionally substituted monocyclic or bicyclic ring with one or more heteroatoms; $R^9$ is independently selected from the group consisting of hydrogen, alkyl, alkenyl, alkynyl, heteraryl, aryl cycloalkyl, wherein the alkyl, alkenyl, heteraryl, aryl and cycloalkyl are optionally substituted with one or more halo, cyano, alkylamino, alkoxy, aryl, heteroaryl or heterocyclyl groups; each $R^{11}$ and $R^{12}$ is independently —H, —COR$^{13}$ or —CH$_3$; and R$^{13}$ is alkyl, haloalkyl, alkenyl, alkynyl, or cycloalkyl.

It should be appreciated that methods of the invention can include administering a compound of formula I alone, mixture comprising two or more of compound of formula II, and compound of formula I with one or more of compounds of formula II. Unless the context requires otherwise, when referring to a compound of the invention, the scope of the invention also includes using a pharmaceutically acceptable salt thereof or a prodrug thereof.

DETAILED DESCRIPTION OF THE INVENTION

Definition: "Alkyl" refers to a saturated linear monovalent hydrocarbon moiety of one to twelve, preferably one to six, carbon atoms or a saturated branched monovalent hydrocarbon moiety of three to twelve, preferably three to six, carbon atoms. Exemplary alkyl group include, but are not limited to, methyl, ethyl, n-propyl, 2-propyl, tert-butyl, pentyl, and the like. "Alkylene" refers to a saturated linear saturated divalent hydrocarbon moiety of one to twelve, preferably one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like. "Aryl" refers to a monovalent mono-, bi- or tricyclic aromatic hydrocarbon moiety of 6 to 15 ring atoms which is optionally substituted with one or more, preferably one, two, or three substituents within the ring structure. When two or more substituents are present in an aryl group, each substituent is independently selected. "Aralkyl" refers to a moiety of the formula —R$^b$R$^c$ where R$^b$ is an alkylene group and R$^c$ is an aryl group as defined herein. Exemplary aralkyl groups include, but are not limited to, benzyl, phenylethyl, 3-(3-chlorophenyl)-2-methylpentyl, and the like. "Cycloalkyl" refers to a non-aromatic, preferably saturated, monovalent mono- or bicyclic hydrocarbon moiety of three to ten ring carbons. The cycloalkyl can be optionally substituted with one or more, preferably one, two, or three, substituents within the ring structure. When two or more substituents are present in a cycloalkyl group, each substituent is independently selected. The terms "cycloalkylalkyl" or "cyclylalkyl" are used interchangeably herein and refer to a moiety of the formula —R$^d$R$^e$ where R$^d$ is an alkylene group and R$^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like. The terms "halo," "halogen" and "halide" are used interchangeably herein and refer to fluoro, chloro, bromo, or iodo. "Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —CH$_2$Cl, —CF$_3$, —CH$_2$CF$_3$, —CH$_2$CCl$_3$, and the like. The terms "heterocyclyl" and "heterocloalkyl" are used interchangeably herein and refer to a non-aromatic monocyclic or bicyclic moiety of three to eight ring atoms in which one or two ring atoms are heteroatoms selected from N, O, or S(O)$_n$ (where n is an integer from 0 to 2), the remaining ring atoms being C, where one or two C atoms can optionally be a carbonyl group. The heterocyclyl ring can be optionally substituted independently with one or more, typically one, two, or three, substituents. When two or more substituents are present in a heterocyclyl group, each substituent is independently selected. Suitable substituents for heterocyclyl group include, but are not limited to, alkyl, haloalkyl, heteroalkyl, halo, nitro, cyano, optionally substituted phenyl, optionally substituted heteroaryl, optionally substituted phenyalkyl, optionally substituted heteroaralkyl, acyl, -(alkylene)$_n$-COOR (n is 0 or 1 and R is hydrogen, alkyl, optionally substituted phenyl, optionally substituted phenyalkyl, or optionally substituted heteroaralkyl), or -(alkylene)$_n$-CONR$^a$R$^b$ (where n is 0 or 1, and R$^a$ and R$^b$ are, independently of each other, hydrogen, alkyl, cycloalkyl, cycloalkylalkyl, hydroxyalkyl, aryl, or R and R' together with the nitrogen atom to which they are attached form a heterocyclyl ring). Exemplary heterocyclyls include, but are not limited to, tetrahydropyranyl, piperidino, piperazino, morpholino and thiomorpholino, thiomorpholino-1-oxide, thiomorpholino-1,1-dioxide, and the like. The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents, preferably one or two substituents, selected from alkyl, haloalkyl, heteroalkyl, heterocyclyl, halo, nitro, cyano, carboxy, acyl, -(alkylene)$_n$-COOR (where n is 0 or 1 and R is hydrogen, alkyl, optionally substituted phenyalkyl, or optionally substituted heteroaralkyl), or -(alkylene)$_n$-CONR$^a$R$^b$ (where n is 0 or 1, and R$^a$ and R$^b$are, independently of each other, hydrogen, alkyl, cycloalkyl, cycloalkylalkyl, hydroxyalkyl, aryl, or R$^a$ and R$^b$ together with the nitrogen atom to which they are attached form a heterocyclyl ring). More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrazinyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like. As used herein, the term "heteroalkyl" means a branched or unbranched, cyclic or acyclic saturated alkyl moiety containing carbon, hydrogen and one or more heteroatoms in place of a carbon atom, or optionally one or more heteroatom-containing substituents independently selected from =O, —OR$^a$, —C(O)R$^a$, —NR$^b$R$^c$, —C(O)NR$^b$R$^c$ and —S(O)$_n$R$^d$ (where n is an integer from 0 to 2). R$^a$ is hydrogen, alkyl, haloalkyl, cycloalkyl, cycloalkylalkyl, heterocyclyl, heterocyclylalkyl, aryl, aralkyl, heteroaryl, heteroaralkyl, or acyl, R$^b$ is hydrogen, alkyl, haloalkyl, cycloalkyl, cycloalkylalkyl, heterocyclyl, heterocyclylalkyl, aryl, aralkyl, heteroaryl, heteroaralkyl, or acyl, R$^c$ is hydrogen, alkyl, haloalkyl, cycloalkyl, cycloalkylalkyl, heterocyclyl, heterocyclylalkyl, aryl, aralkyl, acyl, alkylsulfonyl, carboxamido, or mono- or di-alkylcarbomoyl. Optionally, R$^b$ and R$^c$ can be combined together with the nitrogen to which each is attached to form a four-, five-, six- or seven-membered heterocyclic ring (e.g., a pyrrolidinyl, piperidinyl or morpholinyl ring). R$^d$ ishydrogen (provided that n is 0), alkyl, haloalkyl, cycloalkyl, cycloalkylalkyl, heterocyclyl, heterocyclylalkyl, aryl, aralkyl, heteroaryl, heteroaralkyl, acyl, amino, monsubstituted amino, disubstituted amino, or hydroxyalkyl. Representative examples include, for example, 2-methoxyethyl, benzyloxymethyl, thiophen-2-ylthiomethyl, 2-hydroxyethyl, and 2,3-dihydroxypropyl. "Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, trifluoromethanesulfonyloxy, aryloxy (e.g., 2,4-dinitrophenoxy), methoxy, N,O-dimethylhydroxylamino, tosyloxy, and the like."Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use."Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. The terms "pro-drug" and "prodrug" are used interchangeably herein and refer to any compound which releases an active parent drug (i.e., a compound of the invention such as that of Formula I and/or II in vivo when such prodrug is administered to a mammalian subject. Prodrugs of a compound of the invention are prepared by modifying one or more functional group(s) present in the compound of the invention in such a way that the modification(s) may be cleaved in vivo to release the parent compound. Prodrugs include compounds of the invention wherein a hydroxy, amino, or sulfhydryl group in a compound of the invention is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of the invention, and the like."Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like."Corresponding protecting group" means an appropriate protecting group corresponding to the heteroatom (i.e., N, O, P or S) to which it is attached."A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. As used herein, the term "treating", "contacting" or "reacting" refers to adding or mixing two or more reagents under appropriate conditions to produce the indicated and/or the desired product. It should be appreciated that the reaction which produces the indicated and/or desired product may not necessarily result directly from the combination of two reagents which were initially added, i.e., there may be one or more intermediates which are produced in the mixture which ultimately leads to the formation of the indicated and/or the desired product. As used herein, the terms "those defined above" and "those defined herein" when referring to a variable incorporates by reference the broad definition of the variable as well as preferred, more preferred and most preferred definitions, if any. As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Compounds and Methods of the Invention: Human telomerase reverse transcriptase (hTERT), highly activated in most cancer cells, is involved in telomerase-independent cellular proliferation, apoptosis, DNA damage response, and telomere maintenance. It has been shown that many tumors have transcription-activating mutations in the hTERT core promoter region that form a pair of G-quadruplexes involved in transcriptional silencing. The present inventors have discovered the inhibition of the kinetics of the cooperative folding of activating mutations on the major G-quadruplex structure. This results in a significant change in the percentages of the different species of folded intermediates and final functional form of the silencer element so that the majority of species formed are only the partially folded form. Significantly, compounds that modulate, e.g., reduce or inhibit, hTERT activity has been identified through screening. It is believed that these compounds act as pharmacological chaperones by restoring the correct folding of the active G-quadruplex silencer element so that the percentage of the fully folded form is significantly increased relative to the mutated promoter sequence. Even when mutations are not present, the same molecular chaperones increase the kinetics of folding of the active G-quadruplex silencer element. Thus when the hTERT core promoter is overexpressed due to other genetic changes, the drugs are still effective in lowering hTERT levels. Modulator of hTERT, including a compound named GTC365 herein, directly decreases the transcription activity of the wild-type ("WT") and the −124, −124/125, −138/139, and −146 mutants to a similar extent and suppresses the downstream gene BCL2.Compounds of the invention can also lower the mRNA level of hTERT in melanoma cells that carry the mutations. These compounds have been shown to require the G-quadruplex in the hTERT promoter for activity, and therefore the compounds are selectively toxic toward cells that overexpress hTERT. The present inventors have also discovered that in some instances compounds of the invention, including GTC365, shorten telomere length after five days of treatment, induce a senescence-like phenotype, and activate caspase-3 and cell-cycle arrest, leading to cell death. Compounds belonging to the GTC260 series have similar properties to the GTC365 series and result in lowering of hTERT and BCL2. An important difference between the GTC365 and the GTC260 series is that the GTC260 series lacks the G-quadruplex-interactive moiety but retains the loop-binding moiety, showing that thesepharmacological chaperone properties act at an early point in the cooperative folding process. In addition, these compounds have quite distinct properties tocompounds such as BRACO-19, which act through the G-quadruplexes in the telomeric ends of chromosomes, such as downregulation of BCL2, resulting in apoptosis, and much more potent inhibition of telomerase, resulting in much faster telomere degradation.

One aspect of the invention provides a method for treating a patient suffering from a clinical condition associated with a transcription-activating genetic change associated with the hTERT core promoter region by administering to a patient in need of such a treatment a therapeutically effective amount of compound I, compound II, or a pharmaceutically acceptable salt thereof, or a prodrug thereof, or a mixture thereof. Compounds I and II are of the formula:

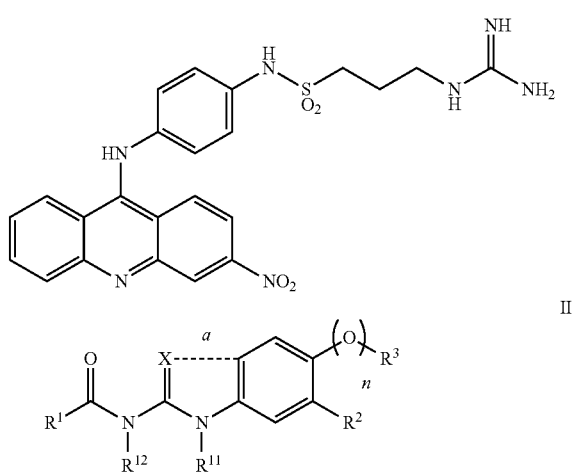

respectively, where X is O or N such that when X is O, bond a is absent and when X is N, bond a is present; n is 0 or 1 such that: when n=0, $R^3$ is —NHC(=NH)NH$_2$; and when n=1, $R^3$ is hydrogen, alkyl, cycloalkyl, optionally substituted heterocycloalkyl, optionally substituted heteroaryl or optionally substituted aryl, wherein each substituent is independently selected from the group consisting of halogen, cyano, nitro, azido, haloalkyl, cycloalkyl, heteroaryl, aryl, —NR$^7$R$^8$, —NR$^7$C(O)R$^8$, —C(O)NR$^7$R$^8$, —C(O)R$^9$, —C(O)OR$^9$, —S(O)R$^9$, —SO$_2$R$^9$, —SO$_2$NR$^7$R$^8$, —OR$^9$ and —SR$^9$; $R^1$ is optionally substituted aryl or optionally substituted heteroaryl, wherein each substituent is independently selected from the group consisting of halogen, cyano, nitro, azido, haloalkyl, cycloalkyl, —NR$^4$R$^5$, —NR$^4$C(O)R$^5$, —C(O)NR$^4$R$^5$, —C(O)R$^6$, —C(O)OR$^6$, —S(O)R$^6$, —SO$_2$R$^6$, - SO$_2$NR$^4$R$^5$, —OR$^6$, and —SR$^6$; $R^2$ is selected from the group consisting of hydrogen, halogen, alkyl, haloalkyl and cycloalkyl; each of $R^4$ and $R^5$ is independently selected from the group consisting of hydrogen, alkyl, alkenyl, alkynyl, heteroaryl, aryl and cycloalkyl, or $R^4$ and $R^5$ together with the nitrogen atom to which they are attached to form an optionally substituted monocyclic or bicyclic ring with one or more heteroatoms; $R^6$ is selected from the group consisting of hydrogen, alkyl, alkenyl, alkynyl, hetearyl, aryl, cycloalkyl, wherein the alkyl, alkenyl, hetearyl, aryl and cycloalkyl are optionally substituted with one or more halo, cyano, alkylamino, alkoxy, aryl, heteroaryl or heterocyclyl groups; each of $R^7$ and $R^8$ is independently selected from the group consisting of hydrogen, alkyl, alkenyl, alkynyl, heteroaryl, aryl and cycloalkyl, or $R^7$ and $R^8$ together with the nitrogen group to which they are attached to form an optionally substituted monocyclic or bicyclic ring with one or more heteroatoms; $R^9$ is independently selected from the group consisting of hydrogen, alkyl, alkenyl, alkynyl, hetearyl, aryl cycloalkyl, wherein the alkyl, alkenyl, hetearyl, aryl and cycloalkyl are optionally substituted with one or more halo, cyano, alkylamino, alkoxy, aryl, heteroaryl or heterocyclyl groups; each $R^{11}$ and $R^{12}$ is independently —H, —COR$^{13}$ or —CH$_3$; and $R^{13}$ is alkyl, haloalkyl, alkenyl, alkynyl, or cycloalkyl.

In some embodiments, the clinical condition associated with the transcription-activating genetic change associated with the hTERT core promoter region comprises a tumor. Within these embodiments, in some instances the tumor comprises brain tumor, bladder cancer, melanoma, thyroid, liver cancer, kidney cancer, stomach, esophagus cancer, lung cancer or neuroblastoma. In one particular instance, the brain tumor comprises glioblastomas.

Another aspect of the invention provides a method for treating a patient suffering from glioblastomas, bladder cancer, melanoma, thyroid, liver cancer, kidney cancer, stomach, esophagus cancer, lung cancer or neuroblastoma by administering a therapeutically effective amount of compound I, compound II, or a pharmaceutically acceptable salt thereof, or a prodrug thereof, or a mixture thereof.

Yet another aspect of the invention provides a method for treating a cancer patient, said method comprising:determining whether a mutation is present in or associated with a hairpin loop of hTERT in a cancer cell of a patient; and when a mutation is present in or associated with the hairpin loop of hTERT in said cancer cell, treating said cancer patient with a therapeutically effective amount of compound I, compound II, or a pharmaceutically acceptable salt thereof, or a prodrug thereof, or a mixture thereof.

In some embodiments, the patient is treated using the method of the invention when the mutation is one of the mutations discussed herein and in the accompanying Figures. In particular, when mutation is present at a location −146, −139, −138, −125,-124 or a combination thereof of the nucleotide sequence of hTERT.

Still another aspect of the invention is directed to a compound of the formula:

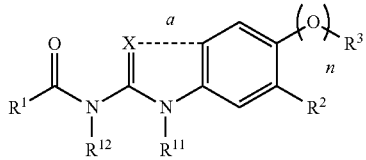

where X is O or N such that when X is O, bond a is absent and when X is N, bond a is present; n is 0 or 1 such that: when n=0, $R^3$ is —NHC(=NH)NH$_2$; and when n=1, $R^3$ is hydrogen, alkyl, cycloalkyl, optionally substituted heterocycloalkyl, optionally substituted heteroaryl or optionally substituted aryl, wherein each substituent is independently selected from the group consisting of halogen, cyano, nitro, azido, haloalkyl, cycloalkyl, heteroaryl, aryl, —NR$^7$R$^8$, —NR$^7$C(O)R$^8$, —C(O)NR$^7$R$^8$, —C(O)R$^9$, —C(O)OR$^9$, —S(O)R$^9$, —SO$_2$R$^9$, —SO$_2$NR$^7$R$^8$, —OR$^9$ and —SR$^9$; $R^1$ is optionally substituted aryl or optionally substituted heteroaryl, wherein each substituent is independently selected from the group consisting of halogen, cyano, nitro, azido, haloalkyl, cycloalkyl, —NR$^4$R$^5$, —NR$^4$C(O)R$^5$, —C(O)NR$^4$R$^5$, —C(O)R$^6$, —C(O)OR$^6$, —S(O)R$^6$, —SO$_2$R$^6$, —SO$_2$NR$^4$R$^5$, —OR$^6$, and —SR$^6$; $R^2$ is selected from the group consisting of hydrogen, halogen, alkyl, haloalkyl and cycloalkyl; each of $R^4$ and $R^5$ is independently selected from the group consisting of hydrogen, alkyl, alkenyl, alkynyl, heteroaryl, aryl and cycloalkyl, or $R^4$ and $R^5$ together with the nitrogen atom to which they are attached to form an optionally substituted monocyclic or bicyclic ring with one or more heteroatoms; $R^6$ is selected from the group consisting of hydrogen, alkyl, alkenyl, alkynyl, heteraryl, aryl, cycloalkyl, wherein the alkyl, alkenyl, heteraryl, aryl and cycloalkyl are optionally substituted with one or more halo, cyano, alkylamino, alkoxy, aryl, heteroaryl or heterocyclyl groups; each of $R^7$ and $R^8$ is independently selected from the group consisting of hydrogen, alkyl, alkenyl, alkynyl, heteroaryl, aryl and cycloalkyl, or $R^7$ and $R^8$ together with the nitrogen group to which they are attached to form an optionally substituted monocyclic or bicyclic ring with one or more heteroatoms; $R^9$ is independently selected from the group consisting of hydrogen, alkyl, alkenyl, alkynyl, heteraryl, aryl cycloalkyl, wherein the alkyl, alkenyl, heteraryl, aryl and cycloalkyl are optionally substituted with one or more halo, cyano, alkylamino, alkoxy, aryl, heteroaryl or heterocyclyl groups; each $R^{11}$ and $R^{12}$ is independently —H, —COR$^{13}$ or —CH$_3$; and $R^{13}$ is alkyl, haloalkyl, alkenyl, alkynyl, or cycloalkyl.

In some embodiments, $R^1$ is selected from the group consisting of:

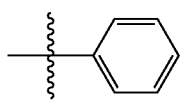 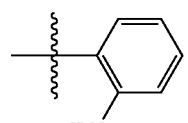

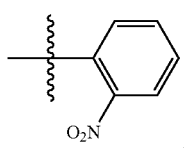 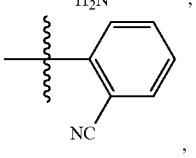

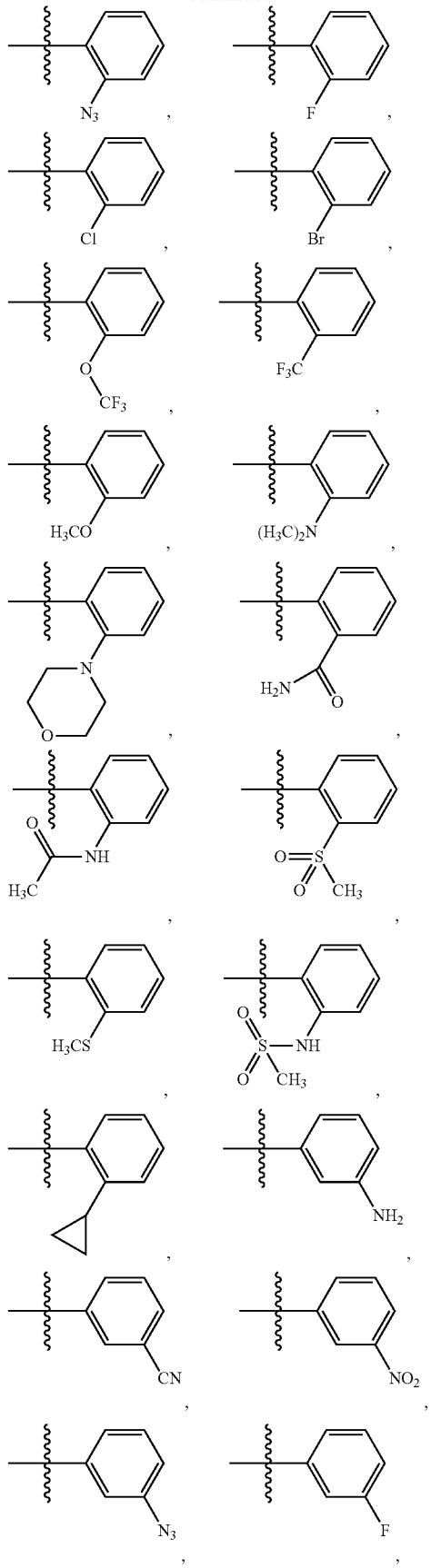

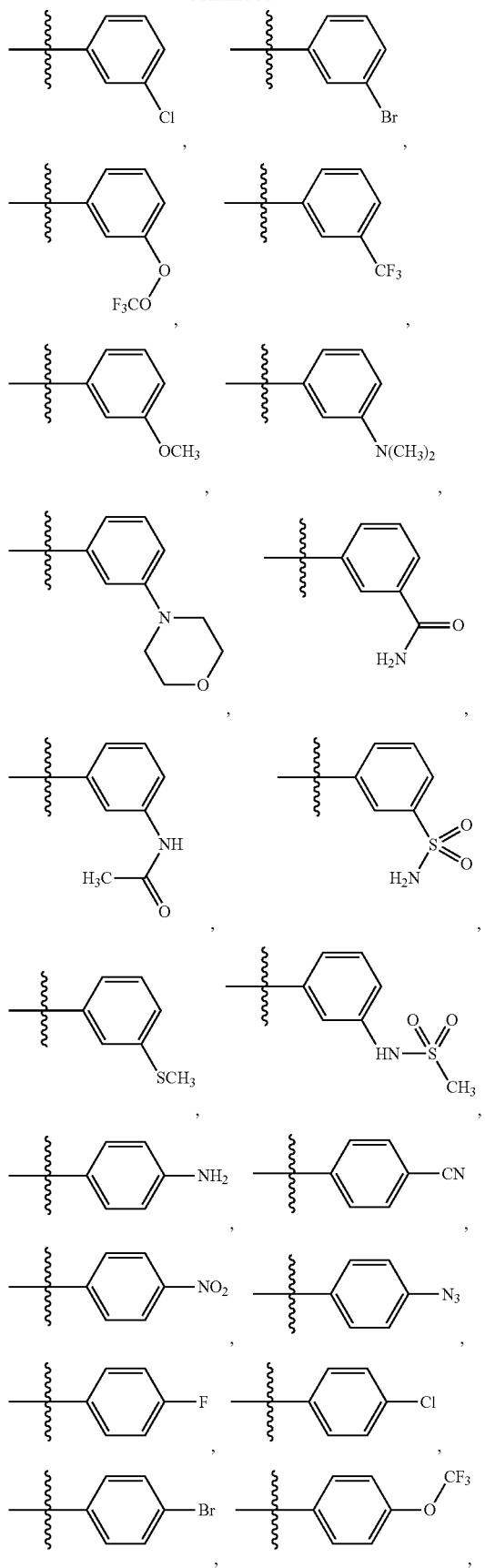
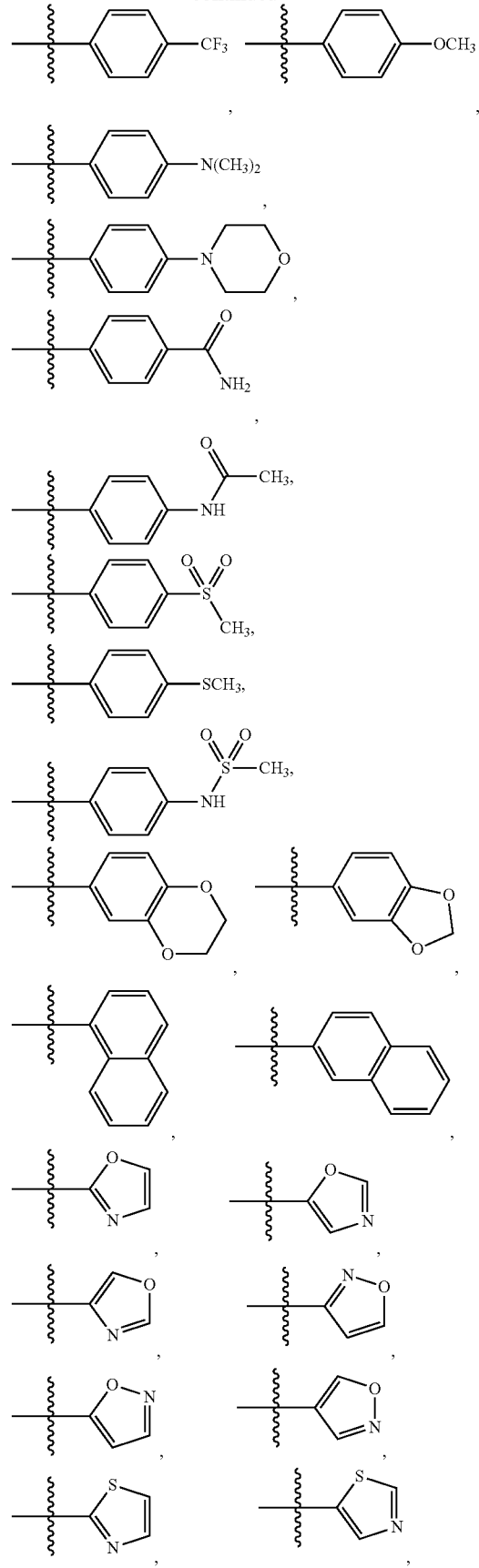

-continued

[chemical structures depicting various heteroaryl moieties including thiazole, isothiazole, pyridine, pyrazine, pyridazine, pyrimidine variants, and substituted pyrimidines with F, Cl, CF₃, NO₂, Br, I substituents]

, and

In another embodiment, R² is selected from the group consisting of hydrogen, methyl, ethyl, isopropyl, trifluoromethyl and a halide.

Still yet in another embodiment, R³ is selected from the group consisting of hydrogen, methyl, ethyl, trifluoromethyl, propyl, cyclopropylmethyl, cyclopentyl, cyclohexyl, benzyl, 2-phenylethyl, 2-methoxyethyl, 3-methoxypropyl, or a moiety selected from the group consisting of:

where m is an integer from 2 to 4; each of $R^{14}$ and $R^{15}$ is independently selected from the group consisting of hydrogen, alkyl, alkenyl, alkynyl, heteroaryl, aryl and cycloalkyl; or $R^{14}$ and $R^{15}$ together with the nitrogen atom to which they are attached to form a substituted or unsubstituted monocyclic or bicyclic heterocycloalkyl.

Some of the representative compounds of Formula II include, but are not limited to, compounds shown on table 1.

TABLE 1
| Compound | R₁ | R₂ | R₃ |
|---|---|---|---|
| GTC260 | 2-NHCOCH(CH₃)NH₂ | —CH₃ | 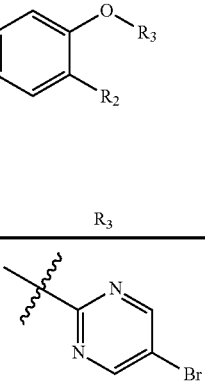 5-bromopyrimidin-2-yl |
| 1 | 2-NH₂ | —CH₃ | 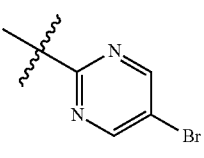 [SMILES: *c1ncc(Br)cn1] 5-bromopyrimidin-2-yl |
| 2 | 2-NH₂ | —CH₃ | —CH₃ |
| 3 | 2-NH₂ | —CH₃ | 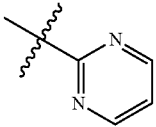 [SMILES: *c1ncccn1] pyrimidin-2-yl |
| 4 | 2-NH₂ | —CH₃ | 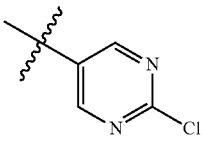 [SMILES: *c1cnc(Cl)nc1] 2-chloropyrimidin-5-yl |
| 5 | 2-NH₂ | —CH₃ | 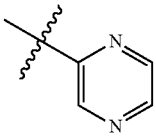 [SMILES: *c1cnccn1] pyrazin-2-yl |
| 6 | 2-NH₂ | —CH₃ | 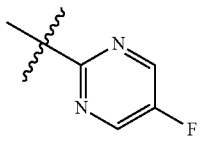 [SMILES: *c1ncc(F)cn1] 5-fluoropyrimidin-2-yl |
| 7 | 2-NH₂ | —H | 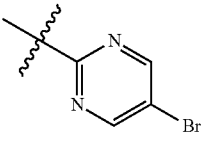 [SMILES: *c1ncc(Br)cn1] 5-bromopyrimidin-2-yl |
| 8 | 2-NH₂ | —H | 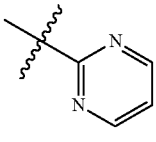 pyrimidin-2-yl |
| 9 | 2-NH₂ | —CH₃ | 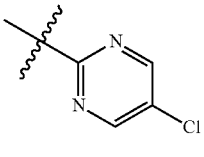 [SMILES: *c1ncc(Cl)cn1] 5-chloropyrimidin-2-yl |

TABLE 1-continued
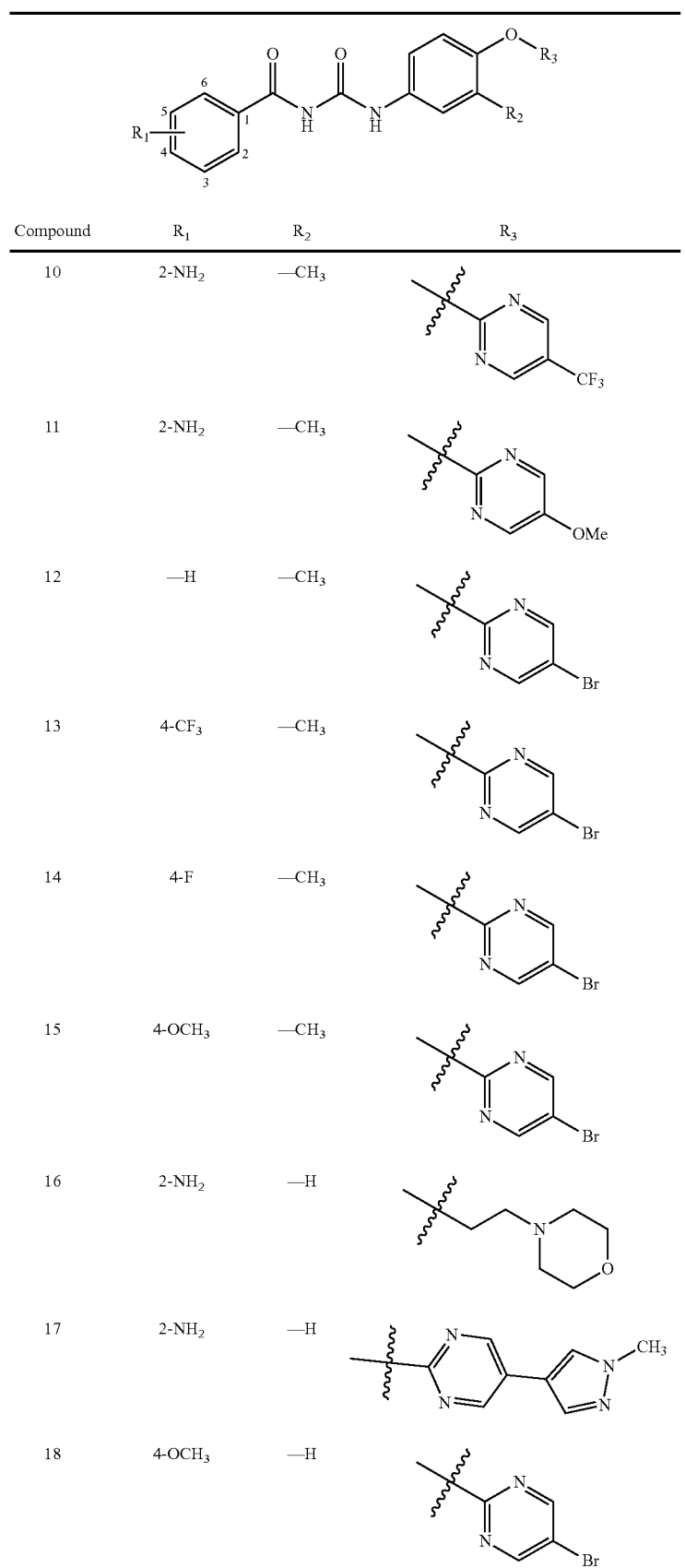
| Compound | R₁ | R₂ | R₃ |
|---|---|---|---|
| 10 | 2-NH₂ | —CH₃ | pyrimidin-2-yl-5-CF₃ |
| 11 | 2-NH₂ | —CH₃ | pyrimidin-2-yl-5-OMe |
| 12 | —H | —CH₃ | pyrimidin-2-yl-5-Br |
| 13 | 4-CF₃ | —CH₃ | pyrimidin-2-yl-5-Br |
| 14 | 4-F | —CH₃ | pyrimidin-2-yl-5-Br |
| 15 | 4-OCH₃ | —CH₃ | pyrimidin-2-yl-5-Br |
| 16 | 2-NH₂ | —H | 3-morpholinopropyl |
| 17 | 2-NH₂ | —H | pyrimidin-2-yl-5-(1-methyl-1H-pyrazol-4-yl) |
| 18 | 4-OCH₃ | —H | pyrimidin-2-yl-5-Br |

TABLE 1-continued
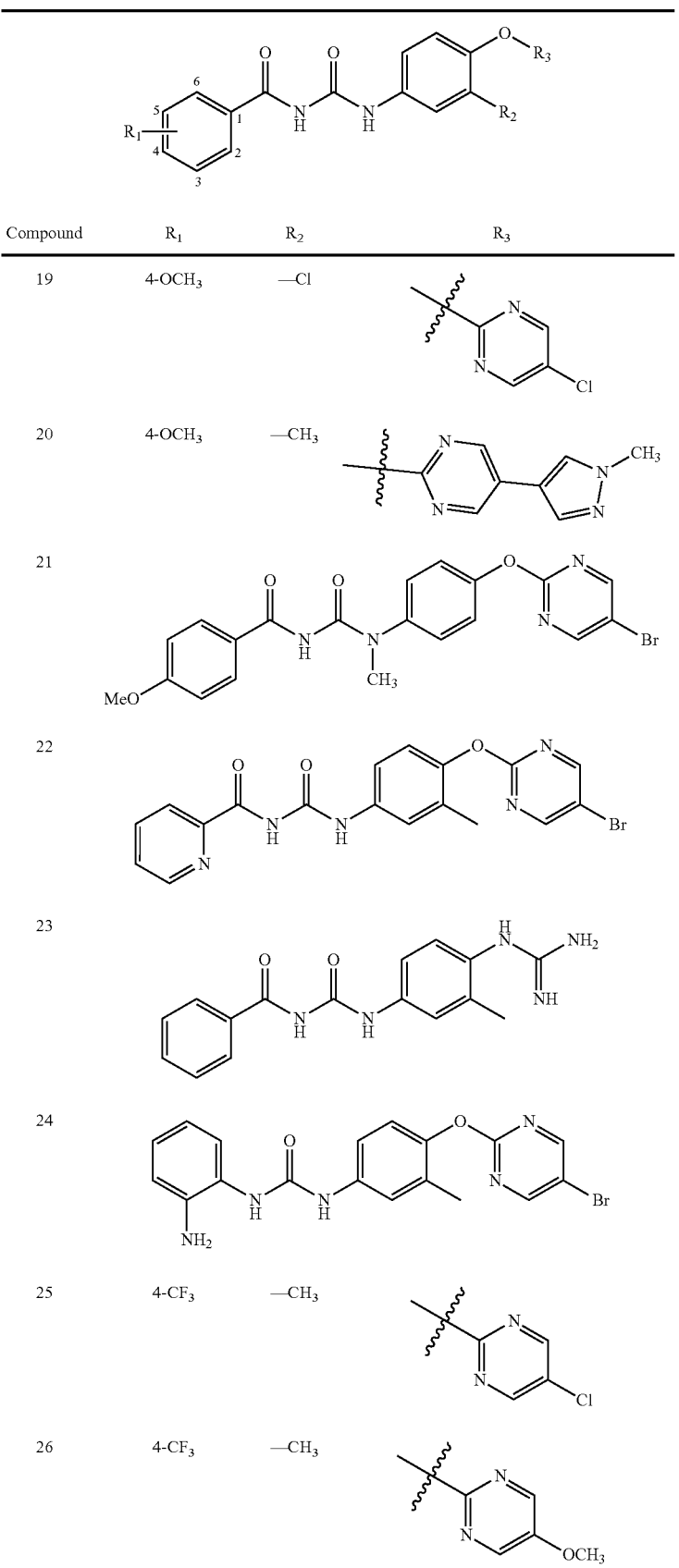
| Compound | R₁ | R₂ | R₃ |
|---|---|---|---|
| 19 | 4-OCH₃ | —Cl | 5-chloropyrimidin-2-yl |
| 20 | 4-OCH₃ | —CH₃ | 5-(1-methyl-1H-pyrazol-4-yl)pyrimidin-2-yl |
| 21 | (full structure shown) | | |
| 22 | (full structure shown) | | |
| 23 | (full structure shown) | | |
| 24 | (full structure shown) | | |
| 25 | 4-CF₃ | —CH₃ | 5-chloropyrimidin-2-yl |
| 26 | 4-CF₃ | —CH₃ | 5-methoxypyrimidin-2-yl |

TABLE 1-continued

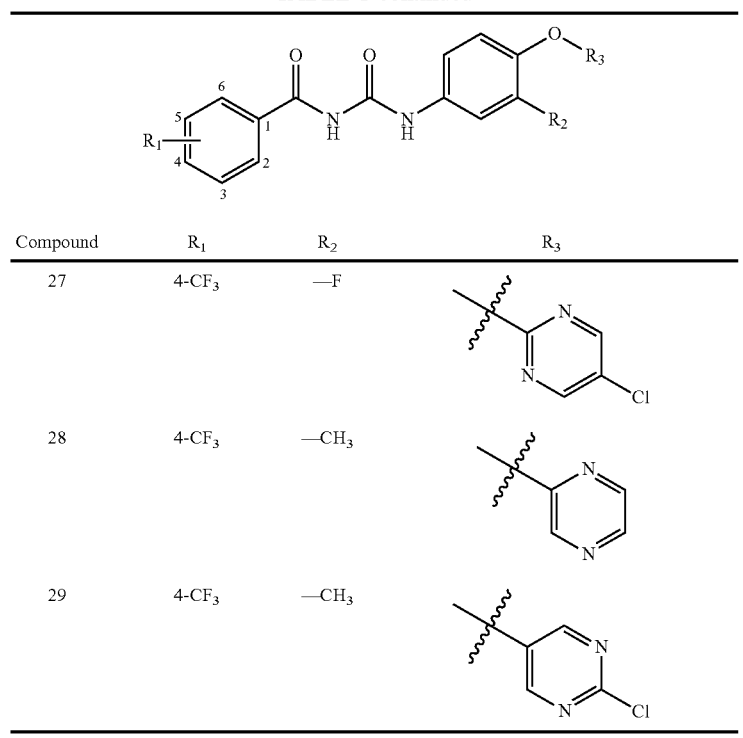

| Compound | R₁ | R₂ | R₃ |
|---|---|---|---|
| 27 | 4-CF$_3$ | —F | (5-chloropyrimidin-2-yl) |
| 28 | 4-CF$_3$ | —CH$_3$ | (pyrazin-2-yl) |
| 29 | 4-CF$_3$ | —CH$_3$ | (2-chloropyrimidin-5-yl) |

It should be appreciated that combinations of various groups described herein form other embodiments. As an illustrative example, compound II can form a wide variety of other compounds of the invention by combining any one of the disclosed X, $R^1$, $R^2$, $R^3$ and n independent of each other. In this manner, a variety of compounds are embodied within the present invention.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Circular dichroism. Oligomers of WT, G124A, G124/125A, G138/139A and G146A were synthesized and HPSF-purified by MGW Operon, Inc. For CD analysis, oligomers (5 μM) in a buffer containing 10 mM Tris-HCl (pH 7.5) and 140 mM KCl were annealed. For the CD analysis of the complex of oligomers and compounds, oligomers (5 μM) in a buffer containing 10 mM Tris-HCl (pH 7.5) and 5 mM KCl for GTC365 or 1 mM KCl for BRACO-19 were annealed. Oligomers and GTC365 or BRACO-19 were incubated overnight at room temperature. For the full-length of C-rich strand, the oligomer in a buffer of 10 mM Na cacodylate (pH 6.6) was annealed and then incubated with GTC365 overnight. CD analysis was conducted on a Jasco 810 spectropolarimeter (Jasco, Easton, Md.) using a quartz cell with 1 mm of path length, 1 nm of band width, and 1 s of response time for spectra at 20° C. Melting curves for the determination of $T_m$ were obtained by recording ellipticity at 262 nm with increasing temperatures from 25° C. to 95° C. at a rate of 1.6° C./min. $T_m$ of the C-rich strand with GTC365 was obtained from the CD signal at 286 nm within 10-60° C.

For the kinetics analysis using the temperature-jump method, theoligo in a buffer containing 10 mM Tris-HCl (pH 7.5) was heated for1 min at 95° C., and then a mixture of KCl and compound was addedand incubated for 1 min. Meanwhile, the CD cuvette was also heatedat 95° C. As soon as the sample in the CD cuvette at the hightemperature was placed in the CD chamber, a time-dependent CDsignal at 262 nm was recorded immediately. The initial folding ratewas determined by one-phase association curve fitting (eq 1) of thekinetics curve using GraphPad Prism 5:

$$Y = Y0 + (\text{Plateau} - Y0)*(1 - e^{-kx}) \quad (1)$$

where Y is the CD signal at any time point x, Y0 is the Y value whentime (x) is zero, plateau is the Y value at infinite time, and k is the rateconstant.

Single-molecule tweezer. Preparation of the DNA construct. The DNA construct that contains the single-stranded hTERT 5-12 fragment was prepared by sandwiching the target sequence between two double-stranded DNA handles. Five deoxythymidines were added at both ends of the hTERT 5-12 fragment to reduce the interference from the double-stranded DNA handles on the target sequence. Briefly, the 2690-base-pair double-stranded DNA handle was prepared through restriction enzyme digestion of the pEGFP vector (Clontech, Mountain View, Calif.). In the first step, the vector was digested by SacI and EagI restriction enzymes, followed by purification with agarose gel. The EagI end of the DNA fragment was labeled with digoxigenin using terminal deoxynucleotidyl transferase. The other double-stranded DNA handle (2028 base pairs) was prepared by PCR using the PBR322 plasmid template and a biotinylated primer. The PCR product was subsequently digested with XbaI restriction enzyme. The middle section that contains the hTERT 5-12 fragment was hybridized from three single-stranded DNA targets. Finally, ligation between the two long double-stranded DNA handles and this double-stranded DNA/single-stranded DNA middle section was achieved using T4 DNA ligase.

To perform the mechanical unfolding experiments, 1 μL of the 2.10 μM polystyrene beads (0.5% w/v) coated with digoxigenin antibody was incubated with 0.1 ng (3.5×10$^{-17}$ mol) of the DNA prepared above in 5 μL of specific buffers (10 mM Tris buffer at pH 7.4 or 50 mM MES buffer at pH 5.5) supplemented with 100 mM KCl or LiCl. After 30 min of incubation, the DNA construct was immobilized on the surface of the beads through affinity interactions. The incubation mixture was diluted to 800 μL with the same buffer for injection into a microfluidic chamber. The DNA construct linked to the 2.10 μMbeads was subsequently tethered to the 1.87 μM polystyrene beads coated by streptavidin through the biotin-labeled DNA construct.

The double-stranded hTERT construct was prepared through a similar strategy. During preparation, two complementary single-stranded DNA oligomers with respective G-rich and C-rich hTERT sequences were annealed to form a double-stranded fragment, which was then ligated with the two double-stranded DNA handles to produce the final target sequence.

Single-molecule force-ramp assay. The laser-tweezers instrument has been described previously.[28] Briefly, a home-build dual-trap laser (1064 nm, 4 W, CW mode, BL-106C, Spectra-Physics) was used as the trapping laser. P- and S-polarized laser light from the same laser source constituted two traps.[28] The mobile laser trap controlled by a motorized mirror grabbed the 2.10 μMbead ligated with target DNA and the other trap grabbed the 1.87 μM bead. While moving the mobile laser trap, the two beads may get close, and a DNA tether can form between them. After this, the two beads were moved apart to increase the tension on the DNA tether with a loading rate of 5.5 pN/s, and the force-extension (F-X) curves were recorded using the LabVIEW program (National Instruments Corp., Austin, Tex.).

The F-X curves were filtered by Savitzky-Golay function with a 10 ms time constant in the MATLAB program (The Math Works, Natick, Mass.). The change in extension (Δx) at a given force was obtained from the subtraction between the stretching and relaxing curves at that force. The change-in-contour length (ΔL) was calculated based on the Δx through the worm-like chain model (equation 1).

$$\frac{\Delta x}{\Delta L} = 1 - \frac{1}{2}\sqrt{\frac{k_B T}{FP}} + \frac{F}{S} \quad (1)$$

where $k_B$ is the Boltzmann constant, T is temperature, P is persistence length (50.8 nm), and S is the stretching modulus (1243 pN) for double-stranded DNA handles.

After calculating ΔL of the structure, the number of nucleotides (nt) contained in a particular length can be estimated based on the ΔL (equation 2):

$$n = \frac{\Delta L + x}{L_{nt}} \quad (2)$$

where x is the end-to-end distance for G-quadruplex or i-motif structures (0.5-1.5 nm) and $L_{nt}$ is the contour length per nucleotide. $L_{nt}$ is located in the range of 0.40-0.45 nm/nt for single-stranded DNA and 0.30-0.35 nm/bp for double-strand DNA.

DMS footprinting. FAM-labeled oligomers (WT, G124A, G124/125A, G138/139A, and G146A) were purchased from MGW Operon Inc. and PAGE purified (Supplementary Table 1). FAM-labeled oligomers (25 nM) were dissolved in a buffer (10 mM Tris-HCl, pH 8.1, and 140 mM KCl) annealed. For the footprinting with GTC365, the methods were modified from the literature.[33] A FAM-labeled oligomer of WT in a buffer containing 50 mM Na cacodylate (pH 7.6) and 5 mM KCl was annealed. GTC365 in 20% DMSO was added to oligomers to produce 1, 2, and 4 equiv. and then incubated at 37° C. for 1 h. For the DMS reaction, oligomers were incubated with 2 μg of salmon sperm DNA (Sigma, D1626) and 5% DMS in 50% ethanol for 8 min. The reaction was stopped by β-mercaptoethanol and then subjected to ethanol precipitation and cleavage by 10% piperidine with incubation at 93° C. for 15 min. Cleaved product was washed twice by water and then separated by 15% denaturing PAGE with 7 M urea. Fluorescence of separated cleavage product was detected by Bio-Rad PharosFX™ Plus, and the band densitogram was obtained by ImageJ.

FRET assay for compound screening and determination of $K_d$ value. FRET probes of WT, G124/125A, and G146A of the 5-12 G-quadruplex were synthesized and labeled with FAM (Ex. 490 nm/Em. 520 nm) and TAMRA (Ex. 560 nm/Em. 580 nm) at each end by MGW Operon Inc. The WT probe (50 nM) was annealed in a buffer containing 10 mM Tris-HCl (pH 7.5) and 5 mM KCl by heating at 95° C. for 5 min and slowly cooling to room temperature. Compounds (50 μM) and probe were incubated for 1 h at room temperature. The same volume of DMSO served as a control. For $K_d$ value determination, the WT, G124/125A, and G146A probes were annealed, and then several concentrations of compound were treated for 1 h at room temperature. Dose-dependent fluorescence intensity at 520 nm was measured by a microplate reader (BioTek Synergy HT). The data were corrected with the blank signal of buffer and compound. The relative fluorescence intensity compared to DMSO was used for binding curve fitting to determine $K_d$ value using Graph-Pad Prism software.

Cell cultures. MCF7 and melanoma (UACC 383) cells were cultured in media of RPMI-1640 with 10% FBS and 1% penicillin/streptomycin. For melanoma cells UACC 2512, UACC 3090, UACC 1729, and UACC 2528, 20% FBS was included in the RPMI media instead of 10% FBS. Cells were incubated at 37° C. with 5% $CO_2$.

qPCR. MCF7 and melanoma cells were treated with GTC365 and BRACO-19 for 72 h. Total RNA was extracted using an RNeasy mini-prep kit (Qiagen) and quantitated by measuring absorbance at 260 nm. cDNA was synthesized using a Takara PrimeScript™ RT Reagent Kit with gDNA eraser and then used as a template for qPCR. The qPCR was performed using Kapa Probe Fast qPCR Master Mix with ABI Taqman probes of hTERT (Hs00972656_m1), BCL2 (HS00608023_m1, FAM-labeled) or MYC (Hs00153408_m1), and GAPDH (Hs02758991_g1, VIC-labeled). The Ct values were measured by running Rotor-Gene Q, and the relative quantity of hTERT, BCL2, and MYC mRNA was obtained compared to GAPDH as an internal control.

Luciferase assay. From gDNA extracted from HeLa cells, the hTERT core promoter region, including −350 bp to +12 from the transcription start site, was amplified using a pair of primers, including KpnI and NheI restriction sites, for cloning of pGL3-hTERT with WT promoter sequence. Mutant constructs were generated by PCR-based site-directed mutagenesis. The sequence of each construct was confirmed by sequencing analysis. MCF7 cells in 24-well plate were transfected with 200 ng of pGL3 construct and 5 ng of pRL-TK by Fugene® HD Transfection Reagent and then incubated for 6 h. Media were replaced by fresh ones and the cells were treated with GTC365 or BRACO-19. The same volume of DMSO served as a control. After 24 h of incubation, cells were lysed by passive lysis buffer (Promega) and subjected to dual-luciferase assay (Promega) using an FB12 luminometer. The ratio of firefly to renilla luciferase activity was normalized to the DMSO to obtain the relative luciferase activity.

Western blot analysis. GTC365- or DMSO-treated MCF7 cells were lysed by RIPA buffer and the supernatant of lysate was obtained by centrifugation at 14,000 rpm for 15 min. The concentration of the whole cellular protein was determined by Bradford assay. The same amount of proteins (120 µg) was separated on 8% SDS-PAGE and transferred to PVDF membrane in 20% MeOH/1× Tris-glycine. The membrane was incubated in a blocking buffer containing 5% BSA/5% non-fat milk with TBS-T (0.1% Tween 20) for 90 min at room temperature prior to overnight incubation with hTERT antibody against rabbit (1:200, Santa Cruz #H231, pAb) in 5% BSA/TBS-T buffer at 4° C. This membrane was incubated with (β-actin antibody against mouse (Cell Signaling #3700, mAb, 1:2,000) for 2 h at room temperature. The membrane was incubated with secondary antibody, goat anti-rabbit IgG (H+L) Dylight 680 (1:7,500), and goat anti-mouse IgG (H+L) Dylight 800 (1:7,500) in 5% non-fat milk/TBS-T for 90 min at room temperature. LI-COR was used to detect the immunocomplex band.

TRAP assay. Compound-treated MCF7 cells were washed withcold D-PBS twice and then collected using a cell scraper. The cellpellet was resuspended in lysis buffer including 10 mM Tris-HCl (pH7.5), 1 mM MgCl2, 1 mM EGTA, 0.5% CHAPS, 10% glycerol, 5 mMβ-mercaptoethanol, 1 Å~protease inhibitor cocktail (Sigma P8340), and 0.2 U/µL of RiboLock RNase Inhibitor (Thermo Fisher, E00381) andkept on ice for 30 min. Supernatant was obtained by centrifugation at14,000 rpm for 20 min, and the concentration of whole protein wasdetermined by Bradford assay. The whole protein was diluted to thesame concentration using the lysis buffer, and 500 ng of whole proteinwas incubated with a mixture of reaction buffer containing 20 mMTris-HCl (pH 8.3), 1.5 mM MgCl2, 63 mM KCl, 0.05% Tween 20, 1mM EGTA, 0.5 µM of TS primer, and 50 µM of dNTPs at 30° C. for 20 min and 95° C. for 2 min for inactivation. As a control reaction, thesame volume of lysis buffer was incubated with the mixture. After thetelomere elongation reaction, the samples were subjected topurification using a Qiagen nucleotide removal kit (#28304) becauseimpurity including compounds in cell lysates can inhibit the PCRreaction.67 The purified samples were completely dried andresuspended with 30 µL of nuclease-free water. For the PCR reaction,1/10 volume of sample was incubated with a mixture of PCR mastermix (Thermo Fisher, K0172), 0.125 U/µL Taq DNA polymerase(Thermo Fisher, EP0402), 62.5 nM TS primer, 62.5 nM ACX primer, and 5 ag of internal standard control (ITAS) in 20 µL. The mixturewas initially incubated at 95° C. for 3 min and then followed by 32 cycles of 95° C. for 30 s, 61° C. for 30 s, and 72° C. for 30 s. The PCRproducts were subjected to 10% Native-PAGE and then stained bySYBR Gold for detection by Bio-Rad Pharos FX. For preparation of ITAS, myogenin 108 nt (Patent application number U.S. Ser. No. 08/423,403)with partial TS and ACX sequence was initially amplified using TS andACX primers to generate 156 bp dsDNA and then purified by gelextraction.

Telomere length assay. MCF7 cells were treated with DMSO, GTC365 for 5-10 days, or BRACO-19 for 25-30 days. Meanwhile, cells were subcultured to maintain <90% confluent. Cells were collected by cell scraper and then subjected to gDNA extraction by DNA extraction kit (Qiagen). Ten ng of gDNA was used for SYBR Green I-based qPCR assay with 1 M betaine, 700 nM telomere primers, and 200 nM 36B4 single-copy gene. A pair of Tel1 and Tel2 was used for amplification of the telomere region and a pair of 36B4F and 36B4R for amplification of a single-copy gene to normalize data. The PCR was initiated at 95° C. for 3 min and then 27 cycles at 95° C. for 3 sec and 60° C. for 2 min. The fluorescence signal at 60° C. was acquired. Triplicate data was averaged and normalized to 36B4 to obtain ΔCt. The relative telomere length was determined compared to the DMSO.

Senescence β-galactosidase assay. A colorimetric β-galactosidase assay was performed. Briefly, compound-treated MCF7 cells were fixed in 2% formaldehyde and 0.2% glutaraldehyde for 5 min at room temperature. Fixed cells were incubated with staining solution containing 40 mM citric acid (pH 6.0), 5 mM potassium ferrocyanide, 5 mM potassium ferricyanide, 150 mM NaCl, and 2 mM $MgCl_2$ and 1 mg/ml X-gal (Fermentas R0401) for 7 h at 37° C. Stained cells were washed with D-PBS and methanol and subsequently dried in air.

Establishment of stable cell lines overexpressing hTERT. The pCDNA-3XHA-hTERT plasmid containing hTERT driven by theCMV promoter was obtained from Addgene (ID: 51637) deposited by Dr. Steven Artandi. MCF7 cells in a 24-well plate were transfected with this plasmid (250 ng) using FuGENE HD transfection reagent for24 h. Cells were treated with several concentrations of G418 (0.1-1 mg/mL) and an antibiotic for colony selection for 4 weeks, and thenone colony was selected for further culture. The expression of ectopichTERT with HA-tag was confirmed by immunoblot analysis usingantibody against HA-tag (Santa Cruz, sc-805, 1:250 in TBS-T bufferwith 5% BSA) as described just below (immunoblot analysis) and qPCR as described above.

Immunoblot analysis. GTC365- or DMSO-treated MCF7 cellswere lysed by RIPA buffer, and the supernatant of the lysate wasobtained by centrifugation at 14,000 rpm for 15 min. The concentration of the whole cellular protein was determined byBradford assay. The same amount of proteins (120 µg for hTERT and50 µg for PARP) was separated on 8% SDS-PAGE and transferred toPVDF membrane in 20% MeOH/1 Å~Tris-glycine. The membrane wasincubated in a blocking buffer containing 5% BSA/5% nonfat milkwith TBS-T (0.1% Tween 20) for 90 min at room temperature priorto overnight incubation with hTERT antibody (1:200, Santa Cruz#H231, pAb) and PARP antibody (1:1000, Cell Signaling #9542) in 5% BSA/TBS-T buffer at 4° C. This membrane was incubated with β-actin antibody against mouse (Cell Signaling #3700, mAb, 1:2,000) for2 h at room temperature. The membrane was incubated withsecondary antibody, goat antirabbit IgG (H+L) DyLight 800(1:7,500), and goat antimouse IgG (H+L) DyLight 680 (1:7,500), depending on the source antibodies, in 5% nonfat milk/ TBS-T for90 min at room temperature. LI-COR was used to detect the immunocomplex band.

Immunofluorescence. TC365-treated MCF7 cells on coverslip were fixed in 2% paraformaldehyde in PBS for 10 min at room temperature and then subjected to permeabilization with 0.2% Triton X-100 in PBS for 10 min at room temperature. Cells were blocked with 4% BSA and 1% non-fat milk in PBS for 1 h at room temperature and then incubated with a-tubulin against mouse (1:200, Cell signaling #3873, mAb) or ZO-1 against rabbit (1:200, Invitrogen #61-7300, pAb) in 20% blocking solution for 1 h. Afterward, cells were treated with secondary antibodies (1:1000, goat-anti mouse Dylight 488 conjugate or goat anti-rabbit IgG Alexa 555 conjugate) in 20% blocking solution for 1 h. Following three washings with PBS, slides were mounted in ProLong Gold Antifade solution with DAPI (Life technologies #P36931). Images were acquired using an Olympus IX71/DP70 digital microscope camera with blue, green, and red filters and then processed with Image Studio Lite (LI-COR Biosciences) and ImageJ.

Caspase assay. MCF7 cells in a 6-well plate were treated with GTC365 for 48 h. The caspase-3 assay was conducted using an Apoalert Caspase 3 Fluorescent Assay Kit (Clontech) with DEVD-AFC as a substrate of capase-3 following the manufacturer's instruction. Fluorescence intensity of released AFC was measured using a BioTek Synergy HT with excitation at 400 nm and emission at 505 nm. The relative caspase-3 activity compared to the DMSO was obtained.

Cell cycle analysis by PI staining. MCF7 cells were treated with GTC365 for 48 h. Cells were trypsinized and washed with cold D-PBS. Cell pellets were subjected to 70% EtOH fixation at −20° C. overnight. Cells were incubated with RNase A and PI for 3 h at 37° C. and then kept in ice before FACS analysis (FACScanto II, BD Biosciences, San Jose, Calif.).

Counting of live cells treated with GTC365. MCF7 cells were treated with DMSO or 0.5 µM of GTC365. Cells were trypsinized and then subjected to trypan blue exclusion staining for counting of live cells using microscopy every three days. Afterward, 70% of cells were recultured with fresh media and DMSO or GTC365. Relative cell numbers compared to the DMSO were obtained.

RESULTS: The somatic mutations of the hTERT core promoter region are found in G-tracts 5, 7, and 8, which have been demonstrated to be part of a G-quadruplex with a unique 3:26:1 loop topology. Based upon DMS footprinting of the full-length oligomer containing all 12 guanine runs, positions −124 and −125 from the ATG site are located in G-tract 5 (G-quadruplex scaffold), −138 and −139 are in G-tract 7 (stem region of hairpin), and −146 is in G-tract 8 (central loop of hairpin). To determine the effect of these mutations on the G-quadruplex structure, circular dichroism (CD), DMS footprinting, and single-molecule laser tweezer experiments were performed.

While the CD spectra of the G146A mutant in the full-length and 5-12 G-rich strands were quite similar to the WT, the G124/125A and G138/139A mutants both showed decreased CD spectra readings. The full-length and 5-12 fragments of G124/125A had melting temperatures ($T_m$) decreased by 1.9° C. and 4.3° C. respectively, and G138/139A showed a similar decrease in $T_m$, of 2.0° C. for the full-length fragment and 3.4° C. for the 5-12 fragment. On the other hand, $T_m$s of G124A and G146A were reduced by 1.5-1.6° C. and 0.9-1.6° C. for both fragments, which is a smaller decrease compared to G124/125A and G138/139A; therefore, additional factors beyond the destabilization of the G-quadruplex might be expected to be important in the overexpression of hTERT.

The present inventors have previously demonstrated that mutations in the hairpin loop result in changes in both the stability and the folding pattern of the G-quadruplex, based upon DMS footprinting. Furthermore, single-molecule laser tweezer experiments showed that the hairpin plays a pivotal role in forming the fully folded species, since mutation resulted in only 4% of the fully folded form. On the basis of these results, it was anticipated that the G124/125A, G138/139A, and, perhaps to a lesser extent, G124A and G146A mutations would change either the folding pattern or the cooperative folding of the WT structure. Importantly, the G124A and G146A mutations, which result in new ETS transcription factor binding sites, are also likely to contribute to the transcription activation. Results showed that WT G-tracts 5, 6, 11, and 12 were protected from DMS cleavage. As anticipated, in comparison to the WT, the footprinting of the G124/G125A mutant showed the greatest changes in the DMS protection pattern, with a loss of protection of G-tracts 7, 9, and 10. In addition, G138/139A and G146A mutants showed more subtle changes in the cleavage of G-tracts in the stem loop, which may represent conformational changes in this part of the structure.

To further understand the influence of the G124/125A mutation on the 5-12 region, single-molecule experiments were conducted on a DNA construct that contains these mutations. First, the effect of the mutation on the DNA secondary structures in the G-rich strand was studied. Although it is more common to use single-stranded G-rich hTERT DNA for this goal, double-stranded DNA in a 10 mM Tris buffer with 100 mM KCl at pH 7.4 was used to allow the formation of only G-quadruplex structures. Given that the 44-nt 5-12 region contains eight G-rich tracts, multiple G-quadruplex populations can exist, each requiring a minimum of four G-rich tracts. Together with partially folded structures, this constitutes a rather complex array of observable structures in single-molecule mechanical unfolding experiments. Through mechanical unfolding of various non-B-DNA structures in a DNA fragment, the present inventorswere able to follow the population dynamics of individual DNA secondary structures with the statistical method PoDNano (Population Deconvolution at Nanometer resolution). With this method, the size of different populations (measured in change in contour length [ΔL]) and their percentages of formation were identified. From a comparison of population patterns of different species, factors such as buffer conditions or mutations can be evaluated. It was observed that the G124/125A mutations dramatically changed the population pattern of G-rich structures, especially for the large species (36 bp and 42 bp), in both single-stranded and double-stranded 5-12 fragments. These species are likely fully folded G-quadruplexes. In addition, the overall formation percentage of G-rich species is reduced compared to the WT DNA. With the same population pattern analysis it was found that the G124/125A mutations do not affect the i-motif population as much as the G-quadruplex, in either the single-stranded or double-stranded DNA construct.

The somatic mutation of the hTERT promoter is proposed to generate an ETS/TCF transcription factor binding site and thus enhance promoter activity. The present inventors have confirmed the increased luciferase activity of all the mutants, in comparison to the WT promoter sequence, using a construct covering −350 to +12 from the transcription start site in MCF7 cells. The extent of enhanced luciferase activity was dependent on the mutated sequences. The G124A, G124/125A, G138/139A, and G146A mutants increased luciferase activity 9.7-, 1.3-, 3.6-, and 3.9-fold, respectively.

Figure 1:
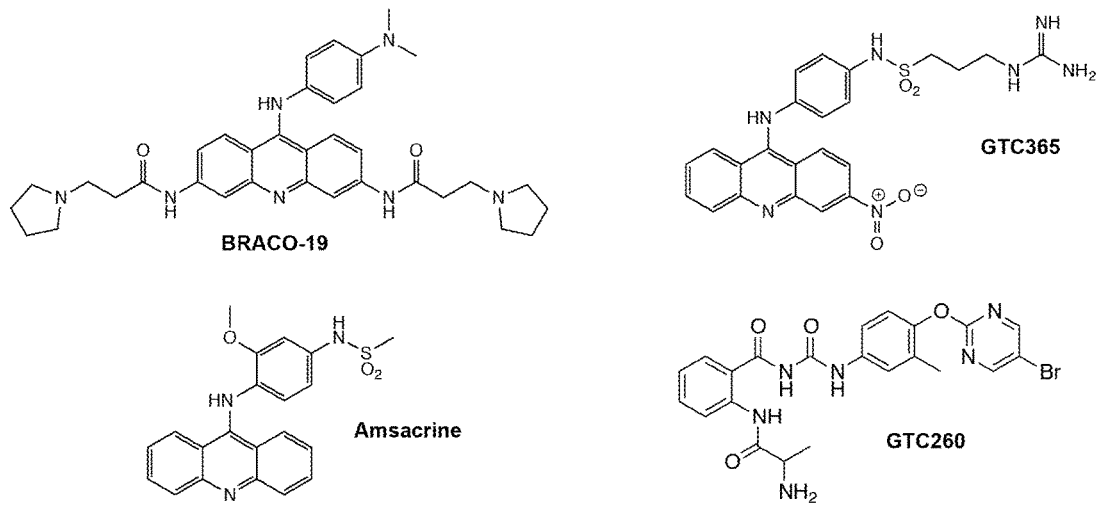
FIG. 1 shows the chemical structures of BRACO-19, GTC365, GTC260, and Amsacrine.
Figure 2:
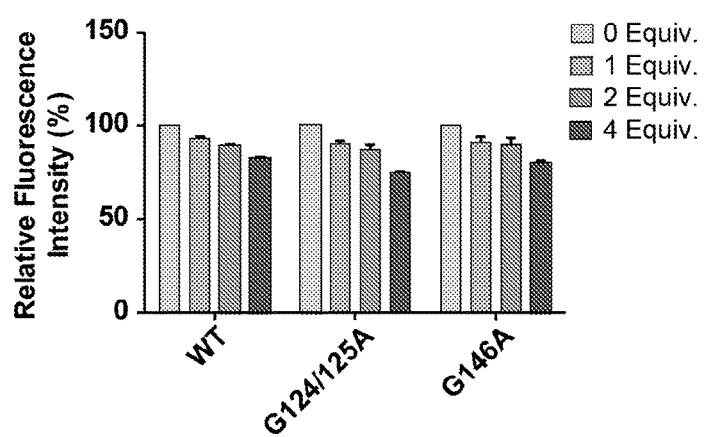
FIG. 2 is a graph showing GTC365 dose-dependent FRET change for WT, G124/125A and G146A.
Figure 3:
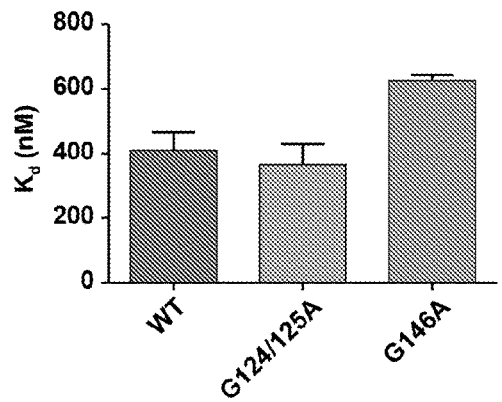
FIG. 3 is a graph showing binding affinity (Kd values) with GTC365 using FAM- and TAMRA-labeled oligomers.

The hTERT core promoter region includes 12 runs of consecutive guanines that form two G-quadruplexes in tandem on the G-rich strand. Since the 5-12 G-quadruplex is primarily responsible for the thermal stability of the full-length structure, this strand was labeled with FAM and TAMRA at each end for the FRET assay. When the G-quadruplex is folded, two fluorophores are in proximity, which leads to a decrease in FAM fluorescence. Using this oligomer, the NCI Diversity Set III (~1500 compounds) was subjected to a FRET assay in a buffer containing 10 mM Tris-HCl (pH 7.4) and 5 mM KCl. Forty-five compounds from the NCI Diversity Set decreased the fluorescence intensity by at least 50%, including compound GTC365, which showed a very significant reduction of fluorescence intensity (94%). Compound GTC260 was identified using a similar strategy. GTC365 is a compound with an acridine scaffold similar to both the telomeric G-quadruplex-binding compound BRACO-19 and Amsacrine, whereas GTC260 lacked the acridine scaffold (FIG. 1). Amsacrine is a topoisomerase II inhibitor used to treat acute lymphocytic leukemia, whereas BRACO-19 is a G-quadruplex-interactive compound that produces telomere shortening, resulting in cellular senescence and cessation of growth after 15 days. GTC365 also showed a dose-dependent decrease of fluorescence intensity of the WT, G124/125A, and G146A probes to a similar extent (FIG. 2). $K_d$ values showed that GTC365 preferentially bound to WT and G124/125A with a similar binding affinity (~400 nM) in contrast to G146A, which showed a 1.5-fold higher $K_d$ value (FIG. 3).

CD and DMS footprinting analyses were conducted to characterize the binding of GTC365 and BRACO-19 to the 5-12 G-quadruplex. CD spectra showed that GTC365 and BRACO-19 both increased the ellipticity at 262 nm with little change at 290 nm. To verify the effects of compounds on the thermal stability of the WT and the mutant G-quadruplexes, $T_m$s were determined by CD. GTC365 dose dependently increased the $\Delta T_m$ of the WT G-quadruplex by 12.9° C. at 2 equiv. The $T_m$s of G124/125A, G138/139A, and G146A mutants were more significantly increased by 6-7° C. compared to the WT, while that of G124A was similar to the WT at 2 equiv. On the basis of these results it was proposed that GTC365 could compensate for thermal instability derived from mutation or low concentrations of KCl. BRACO-19 also significantly increased the $T_m$ of the mutants as well as the WT in a dose-dependent manner. Since acridine derivatives are known to bind to telomeric G-quadruplex, the effects of GTC365 and BRACO-19 on telomeric G-quadruplex stability were compared by CD.

GTC365 showed an increase in $T_m$ for telomeric G-quadruplex, with a $T_m$ of 4.4° C. and 7.5° C. at 1 and 2 equiv., respectively, which is significantly less (42%) than that of the hTERT G-quadruplex. In contrast, BRACO-19 increased the $T_m$ of telomeric G-quadruplex by ~60% compared to that of the hTERT G-quadruplex at 0.5 and 1 equiv. A summary of the comparative $T_m$s of GTC365 and BRACO-19 in hTERT and telomeric DNA is shown below. This demonstrates that GTC365 and BRACO-19 function in opposite ways by selectively binding to the hTERT core promoter G-quadruplex and the telomeric G-quadruplex respectively. There was little change in $T_m$ of the i-motif formed from the full-length C-rich strand by GTC365 suggesting that GTC365 selectively binds to the G-quadruplex over the i-motif.

| $T_m$s Summary: Compound: | GTC365 | | | BRACO-19 | | |
|---|---|---|---|---|---|---|
| Equivalents | 0 | 1 | 2 | 0 | 0.5 | 1 |
| hTERT WT G4 | 0 | 6.47 | 12.92 | 0 | 2.41 | 8.73 |
| Telomeric G4 | 0 | 4.4 | 7.5 | 0 | 4.24 | 14.6 |

To gain some insight into how GTC365 binds to the 5-12 G-quadruplex, the effect of drug binding on the DMS footprint of the WT G-quadruplex-forming sequence was examined. Results showed GTC365 protected the guanine in the 5'-tetrad of G-tract 6 as well as select bases at the 3'-ends in the G-C and G-G base pairing between G-tracts 7 and 10 in the stem. These data suggest that the acridine moiety is positioned on the 5' G-tetrad and the guanidine side-chain interacts with the four G-C and G-G base pairs formed by G-tracts 7 and 10 in the stem. In support of this, it is well known that the guanidinium group of arginine binds to guanines in the major groove of DNA. Thus the larger increase in $\Delta T_m$ of the hTERT G-quadruplex with GTC365 relative to the telomeric G-quadruplex is believed to be due to the additional interactions of the guanidinium with the G-C and G-G base pairs in the hairpin loop.

Single-molecule experiments were used to determine the ability of GTC365 to reverse the effect of the G124/125A mutant on hTERT G-quadruplex stability. After the G124/125A mutant was incubated with 2 µM GTC365 in a 10 mM Tris buffer (100 mM KCl, pH 7.4), in which the formation of a G-quadruplex over an i-motif is favored, it was observed that the full-length G-rich species (>36 nt/bp) recovered in both the single-stranded and double-stranded template. This suggested that GTC365 was acting as a molecular chaperone in facilitating the cooperative folding of the functional G-quadruplex silencer element rather than producing the effects by thermal stabilization of the G-quadruplex.

Figure 4:
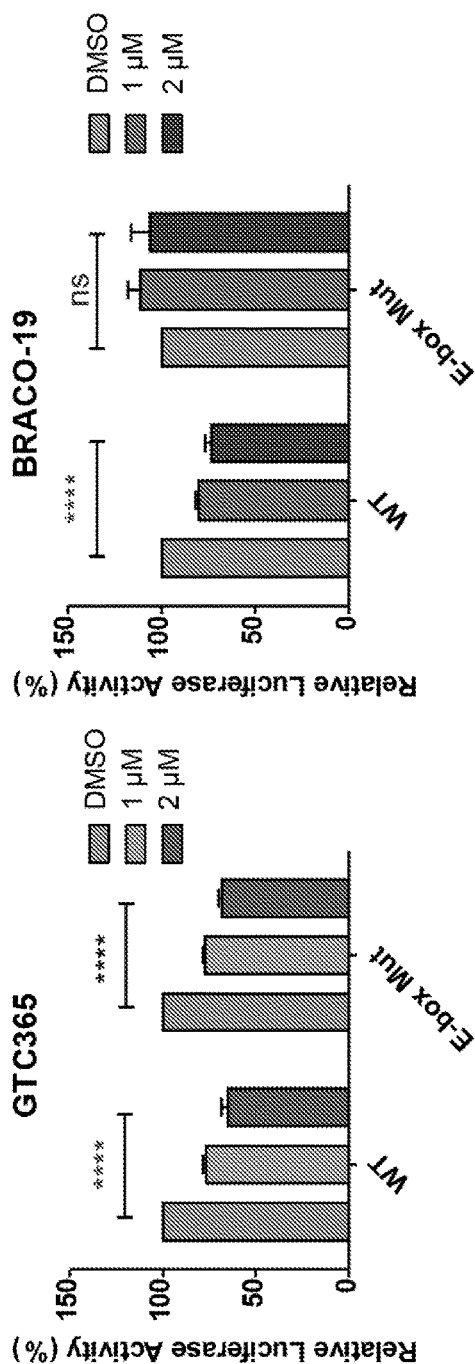
FIG. 4 is a set of graphs showing GTC365 produces direct downregulation of the hTERT core promoter (left) while BRACO-19 downregulation of hTERT is mediated via the MYC G-quadruplex (right), ns=not significant.

Since MYC is a key transcription factor for activation of the hTERT gene by binding to an E-box in the hTERT promoter region and is one of the oncogenes having a G-quadruplex structure in the promoter region, it was important to confirm that GTC365 affects the repression of hTERT promoter activity directly by binding to the G-quadruplex structure formed in the hTERT promoter and not by binding to the G-quadruplex in the MYC promoter. To distinguish between these possibilities, the luciferase activity of the pGL3-WT and pGL3-E-box mutant constructs were determined after treatment with GTC365. As shown in FIG. 4, GTC365 showed a similar dose-dependent decrease of luciferase activity of the WT and E-box Mut construct, which suggests that GTC365 acts predominantly by binding directly to the hTERT G-quadruplex rather than via the MYC G-quadruplex to downregulate transcription of hTERT. In contrast, BRACO-19 decreased luciferase activity of the WT but failed to reduce luciferase activity in the E-box Mut construct. Therefore, it can be concluded that BRACO-19 downregulates hTERT indirectly through binding to the MYC G-quadruplex.

To assess directly whether GTC365 mediates its effects through the hTERT promoter element, we compared the effect of GTC365 on hTERT transcription in MCF7 cells versus similar cells containing a plasmid that overexpresses hTERT but under the control of the CMV promoter. The results show that although GTC365 has a significant effect on hTERT transcription in the MCF7 control cells, where the hTERT promoter is targeted, there was no effect on hTERT transcription in the MCF7 cell line transfected with the plasmid that overexpresses hTERT. The results of this experiment strongly suggest that the molecular target for GTC365 is at the core promoter level rather than a downstream event.

Figure 5:
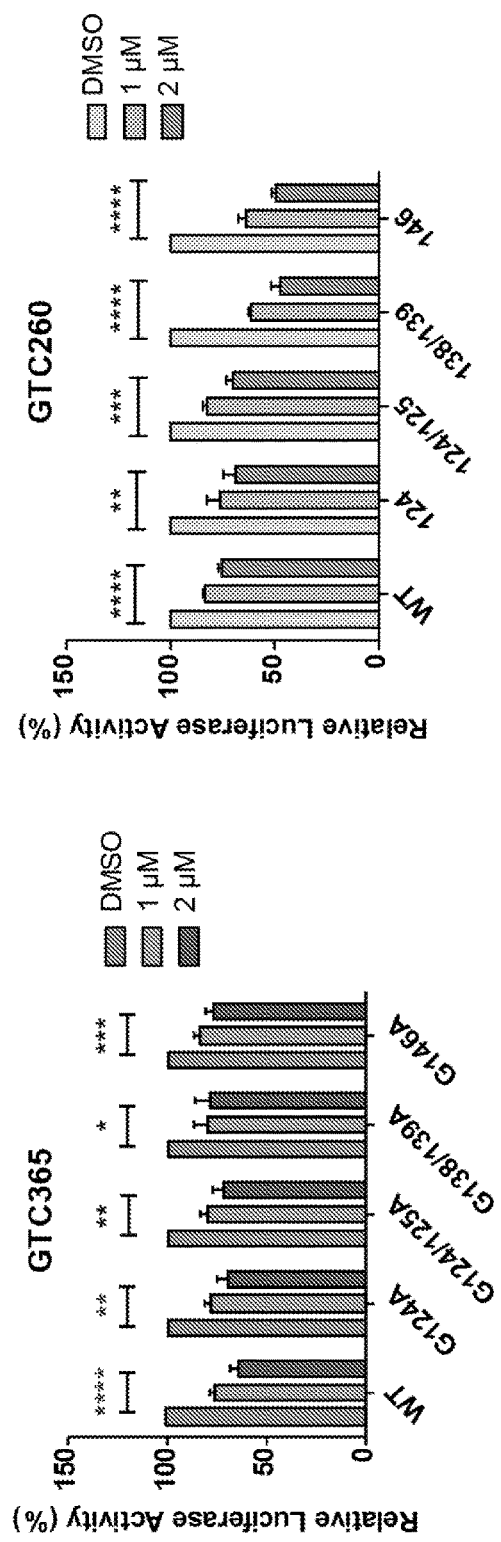
FIG. 5 is a set of graphs showing reversal of mutated promoter activity of hTERT core promoter by GTC365 (left) and GTC260 (right).

The effect of GTC365 on the somatic mutants in the hTERT promoter region was also examined by transfecting cells with pGL3 constructs that contain the G124A, G124/125A, G138/139A, and G146A mutations. As shown in FIG. 5A, GTC365 decreased luciferase activity of the mutants in a dose-dependent manner and therefore acts broadly to downregulate the hTERT promoter activity of the WT and mutants. GTC260 had a similar effect on luciferase activity (FIG. 5B)

Figure 7:
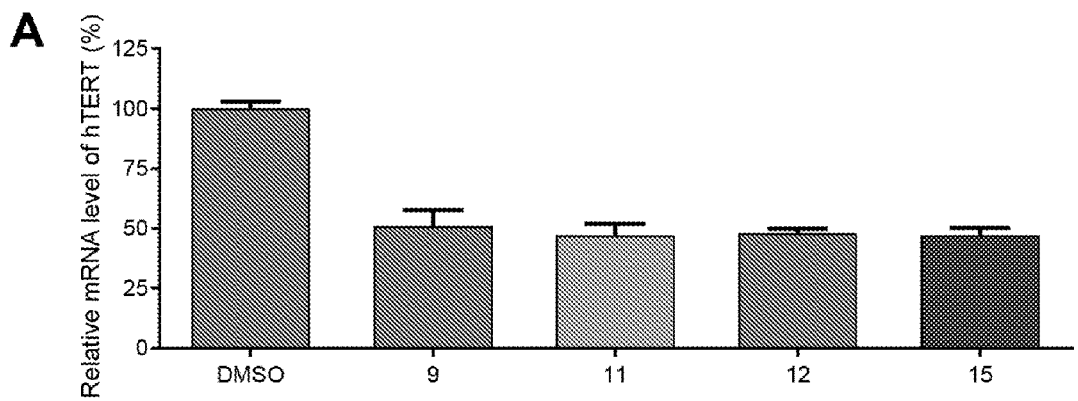
Figure 7:
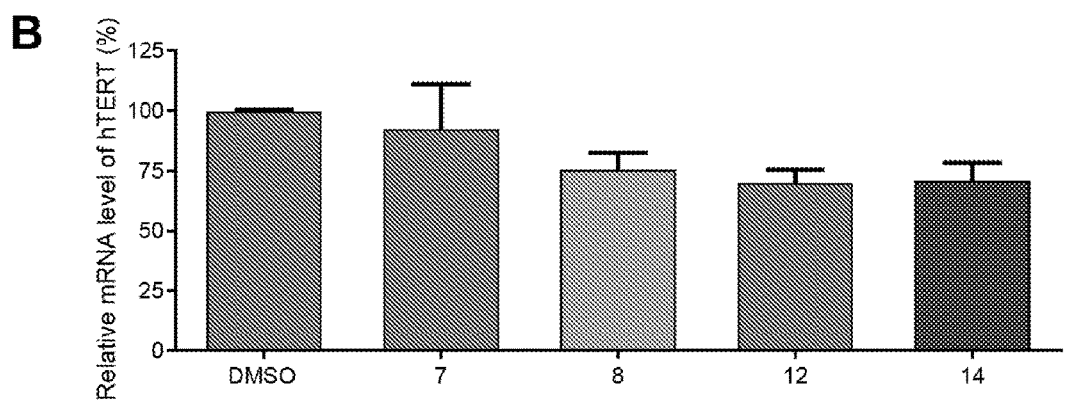
Figure 6:
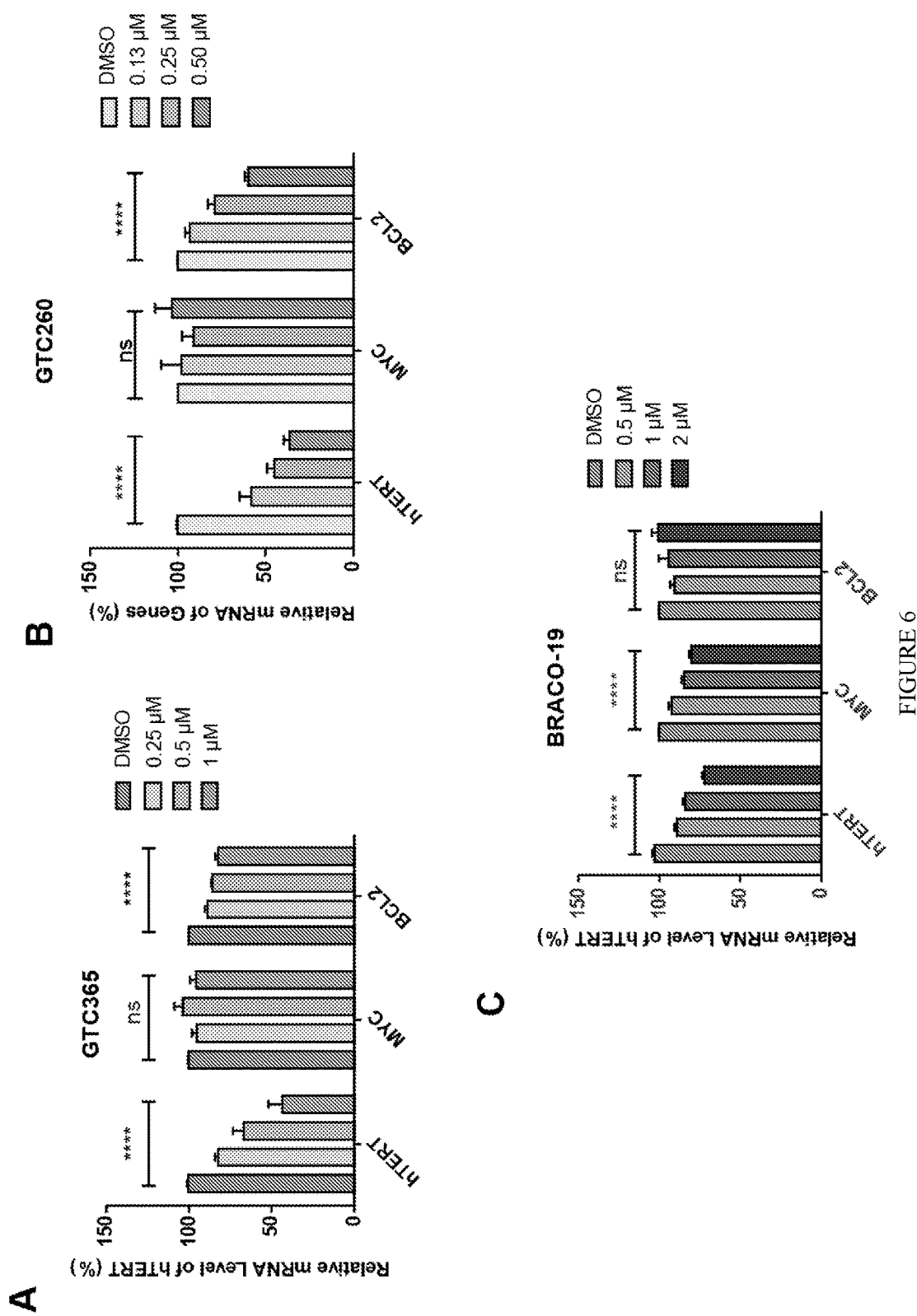
FIGS. 6A-6C are a set of graphs showing (A) GTC365 produces direct repression of hTERT transcription and the downstream molecule BCL2 but has no effect on MYC mRNA level. (B) GTC260 produces direct repression of hTERT transcription and the downstream molecule BCL2 but has no effect on MYC mRNA level. (C) BRACO-19 knocks down MYC and hTERT transcription, but has no significant effect on BCL2 mRNA levels in MCF7 cells after 72 h.

BCL2 is a downstream molecule to hTERT such that BCL2 expression is activated by hTERT to repress apoptosis. To further define the effect of GTC365 on the transcription of hTERT, the relative mRNA levels of MYC and BCL2 were determined by quantitative PCR analysis in MCF7 cells after treatment with GTC365 for 72 h. As shown in FIG. 6A, GTC365 decreased the hTERT mRNA levels in a dose-dependent manner by up to 67% (at 1 µM), and BCL2 mRNA level was also dose-dependently decreased by up to 18% at 1 µM, with no significant change in MYC mRNA levels. GTC260 had a similar effect on hTERT activity (FIG. 6B). A series of GTC260 analogs were synthesized and their effect on hTERT gene expression in MCF7A and U87 cells determined (FIG. 7). In contrast, as shown in FIG. 6C, BRACO-19 decreased mRNA levels of both hTERT and MYC to a similar extent at a somewhat higher concentration range compared to GTC365. Therefore, GTC365 directly repressed the transcription of hTERT and then led to a downstream decrease of BCL2 expression. It was demonstrated using western blot that the protein level of hTERT protein level was also downregulated.

To determine the cellular effect of GTC365 on proliferation as well as suppression of the activation of hTERT by G124A, G124/125A, G138/139A, and G146A mutants, melanoma cell lines were used alongside a WT cell line. All mutants increased the mRNA level of hTERT, compared to WT melanoma cells, in the 6.6-34-fold range. To evaluate the effect of GTC365 on the hTERT mRNA level in melanoma cells, cells were treated with several concentrations of GTC365 for 72 h (FIG. 8). GTC365 showed a similar dose-dependent decrease (25% at 1 µM) in the mRNA level of hTERT in the WT and all mutant cells. GTC365 also decreased the mRNA level of BCL2 in WT and G146A cells as expected. To determine the effect of GTC365 and BRACO-19 on cellular proliferation in melanoma promoter mutant cell lines, an MTS assay was conducted following 72 h treatment. GTC365 and BRACO-19 both showed $EC_{50}$ values in the 18-40 µM range.

hTERT-positive MCF7 breast cancer cell lines were used to gain mechanistic insight into how the GTC365-induced inhibition of proliferation occurs. Change in relative telomere length by GTC365 was measured by qPCR with gDNA extracted from GTC365-treated MCF7 cells. After 10 days of treatment GTC365 decreased telomere length in a dose-dependent manner, and at a dose of 0.5 µM, the telomere length was reduced by 20%. In contrast, BRACO-19 reduced telomere length by ~12% at the same concentration but required 25-30 days of treatment (FIG. 9).

Figure 10:
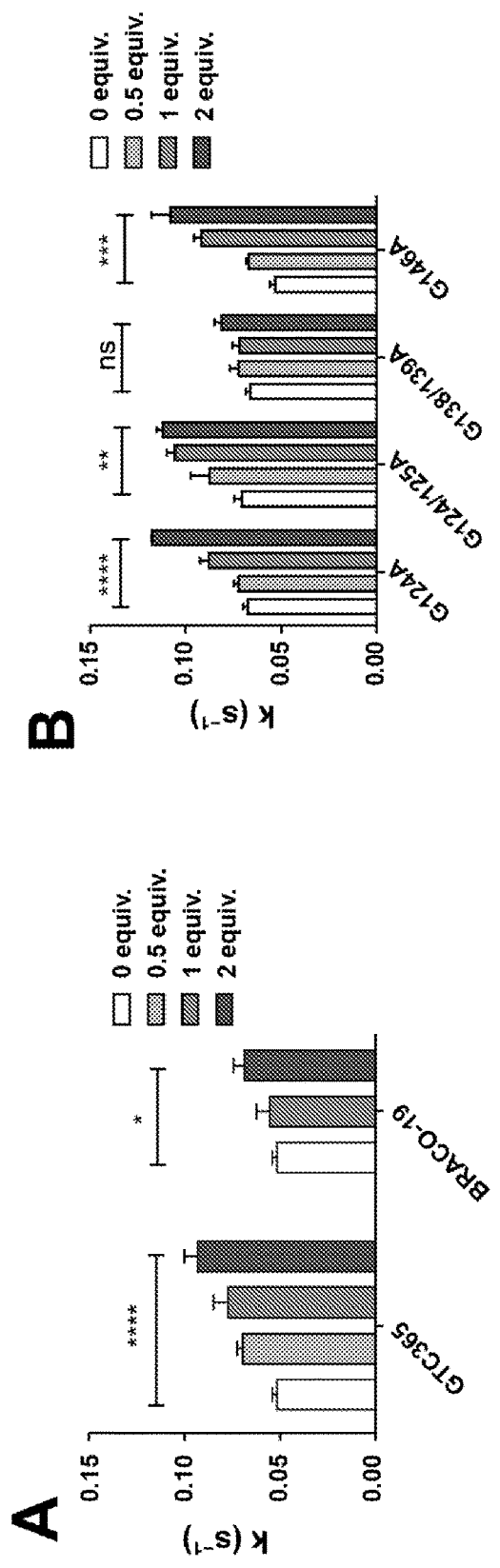

To evaluate the comparative effects of GTC365 relative to BRACO-19 on the cooperative folding process, we carried out two different experiments. First, we compared the distribution of the different populations of small and large species using single-molecule experiments as described previously with GTC365 and BRACO-19 in the G138/139A mutant. Similar to the G124/125A mutant, the population of fully folded structures is small in the G138/139A mutant without addition of ligand. After incubating with 2 µ MGTC365, the fully folded structures significantly recovereddemonstrating the population effect of this ligand to form thefully folded G-quadruplex species. BRACO-19 minimallypromoted the fully folded structure; instead, this molecule increasedpartially folded populations. These results provide a rationale for the discrepancyin the biological activities of GTC365 and BRACO-19.Second, we used CD kinetic analysis to compare the relativerates of initial folding for GTC365 and BRACO-19 in the WT and mutant species with GTC365 (FIG. 10). We then used a temperature-jump method84to compare the initial folding rate of the 5-12 WT G-quadruplex with GTC365 and BRACO-19 using a time-course CD signal curve. As shown in FIG. 10A, the initial folding rate of the 5-12 WT G-quadruplex by GTC365 at 2 equiv was increased from 0.051 to 0.093 $s^{-1}$, showing an increase of 0.042 $s^{-1}$, whereas BRACO-19 showed a much smaller increase (0.017 $s^{-1}$ at 2 equiv). GTC365 alsoincreased the initial folding rates of G124A, G124/125A, andG146A in a dose-dependent manner by 0.049, 0.042, and 0.054$s^{-1}$ at 2 equiv, whereas the effect on the G138/139A mutant was insignificant (FIG. 10B). Taken together, these results strongly suggest that GTC365 and GTC260 both act as pharmacological chaperones by facilitating the cooperative folding of the functional silencer element. This role of these compounds in silencing the transcription activation of hTERT is equally important for treatment of cancers that overexpress hTERT as a consequence of mutation in the core promoter element or other genetic aberrations.

Since senescence is one of the outcomes resulting from loss of telomere length, this was measured by the associated overexpression of lysosomal β-galactosidase, which releases indigo (blue dye) from X-gal. In addition, the cell morphology will also be dramatically changed so that cells appear to be flat and enlarged. The blue-stained MCF7 cells showed a distinct senescence-like phenotype (SLP), and there was significant morphological changes in the cells so that they became flat and enlarged following 5-10 days of treatment with 0.5 µM GTC365. Abnormal phenotypes such as bridges connecting two adjacent cells and multinucleated cells were also observed in GTC365-treated cells. hTERT is known to localize to mitotic spindles and centromeres and regulate the expression of genes involved in heterochromatin maintenance. In addition, there is alteration of expression of some proteins involved in collagen synthesis or tubulin organization by hTERT transfection. This suggests that GTC365 induced failure of mitosis and cytokinesis by downregulation of hTERT.

Previous observation by the present inventors that GTC365 repressed BCL2 expression suggests that there should be an increase in the BAX/BCL2 ratio as well as in caspase-3, the final executor for apoptosis. Indeed at 0.5-1 µM, the BAX/BCL2 ratio was increased by over 2-fold and the capase-3 activity was increased by 47% (FIGS. 11 and 12).

Since knockdown of hTERT arrests the cell cycle in the G0/G1 phase, the effects of GTC365 on the cell cycle were evaluated. GTC365 increased the population of the G0/G1 (from 57% to 71%) and G2/M phases (from 10% to 19%), whereas the S-phase was decreased (from 33% to 10%) in a dose-dependent manner with 48 h treatment. Five days of treatment with GTC365 also showed the same pattern. Therefore it can be inferred that knockdown of hTERT directly induced G0/G1 phase arrest, whereas DNA damage by GTC365 induced G2/M phase arrest. Most of the cells showing SLP underwent cell death with exposure to a low dose of GTC365 in nine days. It is known that various anticancer drugs induce SLP in different cancer cells, leading to mitotic catastrophe as well as apoptotic cell death. Doxorubicin, one of the representative anticancer drugs, induced apoptosis and mitotic catastrophe accompanied by multiple nuclei with SLP. GTC365, like doxorubicin, appears to arrest cell proliferation and induce cell death, apoptosis, or mitotic catastrophe through downregulation of hTERT.

Next, to assess the selectivity of GTC365 for hTERT-dependent cancer cells relative to normal precursorcells, we compared the effects of a range of GTC265concentrations on viability at 72 h in normal humanmelanocytes (NHM-002) relative to those of UACC-903, aG124A mutant (FIG. 13A). Viability was significantly reduced in a dose-dependent manner in melanoma cells, droppingbelow 50% at 5 µM. However, only a minimal viability change was seen in normal melanocytes and was not statistically significant. To confirm that the reduction in cell viability was aresult of hTERT downregulation, we performed reverse transcription and qPCR to measure the mRNA level of hTERT expression in cells treated with DMSO or 5 µMGTC365. hTERT expression was reduced by 41% in themelanoma cell line after 72 h but was undetectable in normalmelanocytes, even in the absence of GTC365 (FIG. 13B). Finally, tobroadly assess the selectivity of GTC365 for hTERT promoter-mutant versus WT cells, we conducted a 6-point 72 h MTSproliferation assay to determine $EC_{50}$s in 14 additional melanoma cell lines with characterized TERT promoter status(19 cell lines in total) (FIG. 13C). GTC365 showed $EC_{50}$values. Ultimately, this broad screen shows a significant differential response toGTC365 between WT and mutant melanoma cell linesand confirms increased GTC365 activity in mutant cellsthat express higher levels of hTERT These datasupport that GTC365 reduces cell proliferation throughdownregulation of hTERT expression via stabilization of theG-quadruplex promoter structure. This mechanism is selective for hTERT-dependent melanomas such as those bearing hTERT promoter mutations.

DISCUSSION: Limitless proliferation potential due to telomerase activation is one of the original hallmarks of cancer, and hTERT is the key component for maintenance of telomerase activity. While telomerase has been the major target for drug therapy designed for destabilization of telomeres by inhibition of telomere elongation or telomere uncapping, the direct repression of hTERT promoter activity has distinct advantages associated with impairing various functions for cell survival as well as telomere maintenance. Without being bound by any theory, some aspects of the invention provide a new strategy involving small molecules to directly target hTERT expression at the promoter level so that short-term effects are seen that result in apoptosis within 48 h and non-apoptotic death within 5-10 days.

Recently it has been shown that specific somatic mutations in the hTERT core promoter element result in a 2-4-fold increase in luciferase activity and that these mutations are commonly found in a number of cancers, most notably melanomas and gliomas, where they are often associated with poor prognosis. In an attempt to rationalize the molecular basis for the transcriptional effects of these somatic mutations of hTERT, it has been proposed that new ETS transcription factor binding sites are generated in the duplex form of the promoter. However, while the G124A mutant, which has the highest transcription activity (9.7-fold), generates an ETS transcription factor binding site, the G124/125A mutantwould be predicted to diminish the affinity of ETS protein. However, conflicting results from others strongly suggest that there must be other factors beyond the duplex sequence information that are required to understand the effects of promoter mutations on the transcription activation of hTERT.

As disclosed herein, the present inventors have shown that the core hTERT promoter sequence forms a tandem set of G-quadruplexes that have been demonstrated to inhibit hTERT transcription when stabilized by compounds that bind to these structures. Furthermore, all the somatic mutation sites found in the hTERT promoter are associated with the 5-12 G-quadruplex. These structural insights provided the present inventors with the opportunity to evaluate (1) whether the presence of potentially destabilizing promoter mutations in the major G-quadruplex silencer element could be used to rationalize the transcription activation observed in tumors bearing these mutations and (2) whether one can identify specific compounds that can reverse the effects of these mutations by stabilizing an otherwise compromised silencer element.

The present inventors have discovered that hTERT expression was enhanced very significantly 6.6-34-fold in the hTERT promoter mutations melanoma cells. The present inventors have also identified, through a FRET screening method compounds that can modulate hTERT, e.g., a guanidine-acridine derivative (GTC365) and a second compound which lacks the acridine but retains the moiety which interacts with the hairpin loop (GTC260). These compound partially reversed the effect of the activating mutations by binding to the duplex stem of the hairpin. The acridine in the GTC365 also binds to the tetrad that is in juxtaposition to the hairpin loop. For comparison the effects of BRACO-19, which has been previously shown to inhibit telomere elongation, were evaluated albeit over an extended period of time (15 days). While GTC365 preferentially stabilized the hTERT G-quadruplex over the telomeric G-quadruplex, BRACO-19 had the reverse selectivity. The cellular consequences of the differential binding of the two acridines to the hTERT promoter versus the telomeric G-quadruplexes were also quite different: GTC365 directly repressed hTERT expression and produced induction of apoptosis through lowering of BCL2, whereas BRACO-19 only exhibited the longer term effects, mediated through targeting the telomeric G-quadruplexes. Thus while GTC365, like BRACO-19, produced telomere shortening, this was much faster than BRACO-19, taking place within 5 days at a significantly lower concentration. The apoptosis induced within 48 h by GTC365 is mediated by lowering of BCL2, a known consequence of hTERT transcription repression. In addition to induction of apoptosis, GTC365 also induced both G0/G1 and G2/M phase arrest and an SLP, leading to non-apoptotic cell death accompanied with abnormal cell division with bridges between cells and multiple nuclei that may both be related to the short-term telomere-shortening effects or uncapping of telomeres, as well as telomere-independent activity of hTERT.

Drug targeting of the hTERT G-quadruplex represents a special case where it is possible to gain selectivity based upon the added complexity of the presence of a large hairpin loop in juxtaposition to one of the external tetrads. In this case the present inventors have shown that GTC365 and BRACO-19 produced different biological consequences based upon their differential binding to the hTERT and telomeric G-quadruplexes.

The present inventors have characterized the destabilizing effect of somatic mutations on the major G-quadruplex, which is the silencer element in the hTERT core promoter region. The guanidine-acridine compound GTC365 was then identified as one of the compounds able to reverse the transcription-activating effect of these mutations by binding to unique features of this secondary DNA structure to partially restore the silencing ability of the mutant G-quadruplexes. In contrast to approaches that target the telomeric structure, the direct targeting of the hTERT promoter element produces biological effects, such as apoptosis, telomere shortening, cell cycle arrest, and failure of cell division leading to non-apoptotic cell death, that can be observed within 2-5 days, which makes this an attractive therapeutic strategy for treating cancer patients with these hTERT mutations or other genetic aberrations.

A cartoon illustrating the proposed effect of somatic mutations on the cooperative folding process, resulting in activation of hTERTtranscription, and how GTC365 is proposed to act as a pharmacoperone to restore the silencer function is shown in. For the WT cooperative folding pathway, the loop of the hairpin is in proximity to a loop in the adjacent G-quadruplex to provide critical tertiary interactions, leading to the functional silencerelement. For illustrative purposes, G146 is shown making this interaction, and G124 is base-paired to C134 at the bottom of the hairpin-loop. In the case of any of the mutant promoter elements, the loss of one of these critical tertiary interactions between the hairpin and the adjacentG-quadruplex, which is required for steering the correct folding pathways, then leads to misfolding of the 5-12 G-quadruplex and a nonfunctionalsilencer element. The binding of the pharmacoperone GTC365 to the mutant hairpin loop restores the folding pathway, leading to afunctional silencer element.

Synthesis of compounds of the invention: Abbreviations used in the present invention: DCM (Dichloromethane); EtOH (Ethanol); DMSO (Dimethyl sulfoxide); DMF (N,N-dimethylformamide); Pd(dppf)$_2$Cl$_2$ [(1,1'-B is(diphenylphosphino)ferrocene)-palladium(II) dichloride]; TFA (Trifluoroacetic acid); TEA (Triethylamine); TLC (Thin layer chromatography); and NMR (Nuclear magnetic resonance).

General Procedure: All the chemicals were purchased from commercial vendors. All the solvents were obtained from Fischer Scientific. Column chromatography was performed with silica gel 230/400 mesh. All anhydrous reactions were carried out under positive pressure of nitrogen. HPLC-MS analyses were performed on a Shimadzu UFLC instrument with a Phenomenex monolithic Onyx 50×2 mm C18 reverse-phase column. HRMS results were obtained on an apex-Qe instrument. All $^1$H-NMR and $^{13}$C-NMR spectra were recorded on a Bruker Avance-III 400 MHz NMR instrument, using deuterated solvents. The spectra are reported in ppm and referenced to deuterated DMSO (2.49 ppm for $^1$H, 39.5 ppm for $^{13}$C) or deuterated chloroform (7.26 ppm for $^1$H, 77 ppm for $^{13}$C). High-resolution mass spectra (HRMS) were acquired on a Bruker 9.4 T Apex-Qh FTICR mass spectrometer. All the microwave assisted reactions were performed using Biotage initiator system. All compounds were analyzed for purity by HPLC using either MS or UV absorbance detectors.

Synthesis of 2-amino-N-((4-((5-bromopyrimidin-2-yl)oxy)-3-methylphenyl)-carbamoyl)benzamide (Compound 1)

Oxalyl chloride (0.25 g) was added to 2-nitrobenzamide i (0.1 g) in toluene at 0° C. The solution was allowed to warm to room temperature, then refluxed with stirring for 24 h. The solvent was evaporated and product 2-nitrobenzoyl isocyanate ii wasused directly without further purification for the next reaction.

A solution of 5-bromo-2-chloropyrimidine (500 mg, 2.6 mmol), 4-amino-2-methylphenol (318 mg, 2.6 mmol), and K$_2$CO$_3$ (714 mg, 5.2 mmol) in dry DMSO (20 mL) was stirred at 120° C. for 2.5 h. After cooling to room temperature, the reaction mixture was poured into water and extracted with ethyl acetate. The organic layer was washed with water, saturated brine and then dried. The organic solvent was evaporated to give a residue that was purified using silica gel column chromatography (ethyl acetate-hexane 1:3) to give 200 mg product 4-((5-bromopyrimidin-2-yl)oxy)-3-methylaniline v.

A solution of 2-nitrobenzoyl isocyanate ii (115 mg, 0.6 mmol) in dry DCM (5 mL) was added dropwise to a solution of 4-((5-bromopyrimidin-2-yl)oxy)-3-methylaniline v (168 mg, 0.6 mmol) in dry 1,4-dioxane (1 mL) with stirring at room temperature. The reaction mixture was stirred for 18 h and then diluted with water. The precipitated solid was collected by filtration and washed with water. The solid was dissolved in ethyl acetate, and the organic layer was washed with (3×30 mL) water, dried and concentrated to give 280 mg of product, N-((4-((5-bromopyrimidin-2-yl)oxy)-3-methylphenyl)carbamoyl)-2-nitrobenzamide vi. $^1$H NMR (400 MHz, DMSO-d6) δ 11.29 (s, 1H), 10.22 (s, 1H), 8.80 (s, 2H), 8.22 (ddd, J=8.1, 1.2, 0.6 Hz, 1H), 7.94-7.88 (m, 1H), 7.83-7.76 (m, 2H), 7.47 (d, J=19.8 Hz, 2H), 7.13 (d, J=8.6 Hz, 1H), 2.08 (s, 3H).

Iron powder (160 mg, 3.0 mmol) was added in portions to a mixture of N-((4-((5-bromopyrimidin-2-yl)oxy)-3-methylphenyl)carbamoyl)-2-nitrobenzamide vi (283 mg, 0.6 mmol) and ammonium chloride (335 mg, 6 mmol) in 20 mL ethanol at 80° C. The reaction mixture was refluxed for 30 min and then cooled to room temperature and diluted with water. The precipitated solid was collected by filtration. The solid was dissolved in excess ethyl acetate and filtered. The filtrate was dried and concentrated to give a residue that was purified by column chromatography (ethyl acetate: hexane 2:3) to give 45 mg compound 2-amino-N-((4-((5-bromopyrimidin-2-yl)oxy)-3-methylphenyl)carbamoyl)benzamide 1. $^1$H NMR (400 MHz, DMSO) δ 10.76 (s, 1H), 10.57 (s, 1H), 8.80 (s, 2H), 7.72 (d, J=8.1Hz, 1H), 7.50 (d, J=3.6 Hz, 2H), 7.26 (td, J=8.4, 1.5 Hz, 1H), 7.13 (d, J=9.4 Hz, 1H), 6.79 (d, J=8.4 Hz, 1H), 6.60-6.56 (m, 3 H), 2.09 (s, 3H); HPLC-MS: Expected: 442 (MH+); Found:442.

Synthesis of 2-amino-N-((4-methoxy-3-methylphenyl)carbamoyl)benzamide (Compound 2)

Compound N-((4-methoxy-3-methylphenyl)carbamoyl)-2-nitrobenzamide was prepared using 2-nitrobenzoyl isocyanate and 4-methoxy-3-methylaniline according to the procedure described above. $^1$H NMR (400 MHz, DMSO-d6) δ 11.23 (s, 1H), 10.07 (s, 1H), 8.20 (d, J=8.0 Hz, 1H), 7.89 (td, J=7.5, 1.2 Hz, 1H), 7.83-7.74 (m, 2H), 7.40-7.28 (m, 2H), 6.91 (d, J=8.7 Hz, 1H), 3.78 (s, 3H), 2.16 (s, 3H).

2-Amino-N-((4-methoxy-3-methylphenyl)carbamoyl) benzamide (Compound 2) was prepared using procedure similar to the synthesis of compound 1. $^1$H NMR (400 MHz, DMSO) δ 10.60 (s, 1H), 10.48 (s, 1H), 7.71 (d, J=8.1, 1H), 7.39 (dd, J=8.7, 2.6 Hz, 1H), 7.33 (d, J=2.2 Hz, 1H), 7.24 (td, J=4.8, 3.5 Hz, 1H), 6.91 (d, J=8.8 Hz, 1H), 6.79 (dd, J=8.3, 0.9 Hz, 1H), 6.63-6.45 (m, 3H), 3.78 (s, 3H), 2.17 (s, 3H). HPLC-MS: Expected: 300 (MH+); Found: 300.

Synthesis of 2-amino-N-((3-methyl-4-(pyrimidin-2-yloxy)phenyl)carbamoyl)-benzamide (Compound 3)

3-Methyl-4-(pyrimidin-2-yloxy)aniline was prepared using 2-chloropyrimidine and 4-amino-2-methylphenol according to the procedure described above.

N-((3-Methyl-4-(pyrimidin-2-yloxy)phenyl)carbamoyl)-2-nitrobenzamide was prepared using 3-methyl-4-(pyrimidin-2-yloxy)aniline and 2-nitrobenzoyl isocyanate according to the procedure described above. $^1$H NMR (400 MHz, DMSO-d6) δ 8.64 (d, J=4.8 Hz, 2H), 8.24-8.20 (m, 1H), 7.93-7.88 (m, 1H), 7.83-7.77 (m, 2H), 7.49 (d, J=2.4 Hz, 2H), 7.26 (t, J=4.8 Hz, 1H), 7.10 (d, J=8.6 Hz, 1H), 2.07 (s, 3H).

2-Amino-N-((3-methyl-4-(pyrimidin-2-yloxy)phenyl) carbamoyl)benzamide (Compound 3) was prepared according to the procedure described for the synthesis of compound 1. $^1$H NMR (400 MHz, DMSO) δ 10.76 (s, 1H), 10.57 (s, 1H), 8.64 (d, J=4.8 Hz, 2H), 7.72 (dd, J=8.1, 1.4 Hz, 1H), 7.49 (dd, J=6.1, 2.8 Hz, 2H), 7.31-7.22 (m, 2H), 7.10 (d, J=9.4 Hz, 1H), 6.79 (dd, J=8.4, 1.1 Hz, 1H), 6.56 (m, 3H), 2.08 (s, 3H). HPLC-MS: Expected: 364 (MH+); Found: 364.

Synthesis of 2-amino-N-((4-((2-chloropyrimidin-5-yl)oxy)-3-methylphenyl)-carbamoyl)benzamide (Compound 4)

Compound 4-((5-fluoropyrimidin-2-yl)oxy)-3-methylaniline xi and 4-((2-chloropyrimidin-5-yl)oxy)-3-methylaniline xii were prepared using the procedure described for the synthesis of compound v. Products xi and xii were separated using ethyl acetate: hexane (1:3) column chromatography. For compound xi: $^1$H NMR (400 MHz, Chloroform-d) δ 8.39 (s, 2H), 6.88 (d, J=8.4 Hz, 1H), 6.59-6.57 (m, 1H), 6.56-6.52 (m, 1H), 3.67 (s, 2H), 2.09 (s, 3H). For compound xii: $^1$H NMR (400 MHz, Chloroform-d) δ 8.20 (s, 2H), 6.77 (d, J=8.5 Hz, 1H), 6.59-6.57 (m, 1H), 6.52 (dd, J=8.5, 2.8 Hz, 1H), 3.73 (s, 2H), 2.08 (s, 3H).

Compound N-((4-((2-chloropyrimidin-5-yl)oxy)-3-methylphenyl)carbamoyl)-2-nitrobenzamide xiii was prepared according to the procedure described for the synthesis of compound vi. $^1$H NMR (400 MHz, DMSO-d6) δ 11.30 (s, 1H), 10.25 (s, 1H), 8.49 (s, 2H), 8.22 (ddd, J=8.1, 1.2, 0.4 Hz, 1H), 7.90 (dd, J=7.5, 1.2 Hz, 1H), 7.83-7.75 (m, 2H), 7.56 (s, 1H), 7.49 (d, J=9.2 Hz, 1H), 7.12 (d, J=8.8 Hz, 1H), 2.21 (s, 3H).

2-Amino-N-((4-((2-chloropyrimidin-5-yl)oxy)-3-methylphenyl)carbamoyl)-benzamide (Compound 4) was prepared according to the procedure described above for the synthesis of compound 1 using compound xiii. $^1$H NMR (400 MHz, DMSO-d6) δ 10.80 (s, 1H), 10.58 (br, 1H), 8.49 (s, 2H), 7.72 (d, J=8.1 Hz, 1H), 7.57 (d, J=1.5 Hz, 1H), 7.55-7.49 (dd, J=8.1, 1.5 Hz, 1H), 7.25 (dt, J=8.5, 7.0 Hz, 1H), 7.12 (d, J=8.7 Hz, 1H), 6.79 (d, J=8.5Hz, 1H), 6.57 (br, 2H), 6.55 (dt, J=8.5, 1.5 Hz, 1H), 2.22 (s, 3H). HPLC-MS: Expected: 398 (MH+); Found: 398.

Synthesis of 2-amino-N-((3-methyl-4-(pyrazine-2-yloxy)phenyl)carbamoyl)-benzamide (Compound 5)

Compound 3-methyl-4-(pyrazin-2-yloxy)aniline xv was prepared according to the procedure described above using 2-chloropyrazine and 4-amino-2-methylphenol. $^1$H NMR (400 MHz, Chloroform-d) δ 8.39 (d, J=1.4 Hz, 1H), 8.22 (d, J=2.7 Hz, 1H), 8.10 (dd, J=2.7, 1.4 Hz, 1H), 6.88 (d, J=8.4 Hz, 1H), 6.63 (d, J=2.8 Hz, 1H), 6.58 (d, J=8.4 Hz, 1H), 3.64 (s, 2H), 2.10 (s, 3H).

Compound N-((3-methyl-4-(pyrazine-2-yloxy)phenyl) carbamoyl)-2-nitrobenzamide xvi was prepared using 2-nitrobenzoyl isocyanate and 3-methyl-4-(pyrazin-2-yloxy)aniline according to the procedure described above. $^1$H NMR (400 MHz, DMSO-d6) δ 11.29 (s, 0H), 10.23 (s, 0H), 8.56 (d, J=1.4 Hz, 1H), 8.36 (d, J=2.7 Hz, 1H), 8.24-8.20 (m, 1H), 8.18 (dd, J=2.7, 1.4 Hz, 1H), 7.94-7.88 (m, 1H), 7.80 (td, J=7.7, 1.3 Hz, 2H), 7.51 (d, J=2.6 Hz, 1H), 7.47 (d, J=8.8 Hz, 1H), 7.12 (d, J=8.6 Hz, 1H), 2.10 (s, 3H).

2-Amino-N-((3-methyl-4-(pyrazine-2-yloxy)phenyl)carbamoyl)benzamide (Compound 5) was prepared according to the procedure described for the synthesis of compound 1 using compound xvi. $^1$H NMR (400 MHz, DMSO-d6) δ 10.77 (s, 1H), 10.57 (s, 1H), 8.56 (d, J=1.4 Hz, 1H), 8.36 (d, J=2.7 Hz, 1H), 8.18 (dd, J=2.7, 1.4 Hz, 1H), 7.72 (dd, J=8.1, 1.5 Hz, 1H), 7.52-7.49 (m, 2H), 7.26 (dt, J=8.4, 7.0 Hz, 1H), 7.10 (d, J=8.0 Hz 1H), 6.79 (dd, J=8.4, 1.1 Hz, 1H), 6.65-6.51 (m, 3H), 2.10 (s, 3H). Expected: 364 (MH+); Found: 364.

Compound 6: Compound N-((4-((5-fluoropyrimidin-2-yl)oxy)-3-methyl-phenyl)carbamoyl)-2-nitrobenzamide xvii was prepared according to the procedure described for the synthesis of compound vi. $^1$H NMR (400 MHz, DMSO-d6) δ 11.30 (s, 1H), 10.25 (s, 1H), 8.70 (s, 2H), 8.22 (ddd, J=8.1, 1.2, 0.4 Hz, 1H), 7.90 (dd, J=7.5, 1.2 Hz, 1H), 7.83-7.75 (m, 2H), 7.56 (s, 1H), 7.49 (d, J=9.2 Hz, 1H), 7.12 (d, J=8.8 Hz, 1H), 2.21 (s, 3H).

Compound 2-amino-N-((4-((5-fluoropyrimidin-2-yl)oxy)-3-methylphenyl)-carbamoyl)benzamide 6 was prepared according to the procedure described for the synthesis of compound 1. $^1$H NMR (400 MHz, DMSO-d6) δ 10.76 (s, 1H), 10.56 (br, 1H), 8.73 (s, 2H), 7.72 (d, J=8.1 Hz, 1H), 7.52-7.46 (m, 2H), 7.26 (dt, J=8.4, 7.0Hz, 1H), 7.11 (d, J=9.4 Hz, 1H), 6.80 (d, J=8.4 Hz, 1H), 6.58-6.54 (m, 3H), 2.09 (s, 3H). Expected: 382 (MH+); Found: 382.

Compound 7: Compound 4-((5-bromopyrimidin-2-yl)oxy)aniline xix was prepared using 5-bromo-2-chloropyrimidine and 4-aminophenol according to the procedure described for the synthesis of compound v. $^1$H NMR (400 MHz, Chloroform-d) δ 8.57 (s, 2H), 7.01-6.95 (dd, J=8.4, 1.2 Hz, 2H), 6.76-6.70 (dd, J=8.4, 1.2 Hz, 2H), 3.70 (s, 2H).

Compound N-((4-((5-bromopyrimidin-2-yl)oxy)phenyl) carbamoyl)-2-nitrobenzamide xx was prepared using 2-nitrobenzoyl isocyanate and 4-((5-bromopyrimidin-2-yl)oxy) aniline according to the procedure described for the synthesis of compound vi. $^1$H NMR (400 MHz, DMSO-d6) δ 11.30 (s, 1H), 10.25 (s, 1H), 8.81 (s, 2H), 8.27-8.17 (m, 1H), 7.95-7.88 (m, 1H), 7.84-7.75 (m, 2H), 7.64-7.57 (m, 2H), 7.26-7.18 (m, 2H).

Compound 2-amino-N-((4-((5-bromopyrimidin-2-yl)oxy)phenyl)carbamoyl)-benzamide 7 was prepared according to the procedure described for the synthesis of compound 1. $^1$H NMR (400 MHz, DMSO-d6) δ 10.78 (s, 1H), 10.58 (br, 1H), 8.81 (s, 2H), 7.72 (dd, J=8.1, 1.5 Hz, 1H), 7.68-7.60 (m, 2H), 7.29-7.18 (m, 3H), 6.80 (dd, J=8.4, 1.2 Hz, 1H), 6.56 (dt, J=8.1, 1.2 Hz, 1H). Expected: 428 (MH+); Found: 428.

Compound 8: Compound 4-(pyrimidin-2-yloxy)aniline xxi was prepared using 2-chloropyrimidine and 4-aminophenol according to the procedure described for the synthesis of compound v. $^1$H NMR (400 MHz, Chloroform-d) δ 8.56 (d, J=4.8 Hz, 1H), 7.03-6.99 (m, 2H), 6.76-6.72 (dd, J=8.2 Hz, J=4.8 Hz, 1H).

Compound 2-nitro-N-((4-((pyrimidin-2-yloxy)phenyl) carbamoyl)benzamide xxii was prepared using 2-nitrobenzoyl isocyanate and 4-(pyrimidin-2-yloxy)aniline according to the procedure described for the synthesis of compound vi. $^1$H NMR (400 MHz, DMSO-d6) δ 11.30 (s, 1H), 10.25 (s, 1H), 8.81 (d, J=4.8 Hz, 2H), 8.222 (d, J=8.2 Hz, 1H), 7.95-7.88 (m, 1H), 7.84-7.75 (m, 2H), 7.64-7.57 (m, 2H), 7.26-7.18 (m, 2H).

Compound 2-amino-N-((4-(pyrimidin-2-yloxy)phenyl) carbamoyl)benzamide 8 was prepared from 2-nitro-N-((4-(pyrimidin-2-yloxy)phenyl)carbamoyl)benzamide according to the procedure described for the synthesis of compound 1. $^1$H NMR (400 MHz, DMSO-d6) δ 10.77 (s, 1H), 10.58 (s, 1H), 8.65 (d, J=4.8 Hz, 2H), 7.72 (dd, J=8.1, 1.5 Hz, 1H), 7.68-7.59 (m, 2H), 7.30-7.23 (m, 2H), 7.23-7.16 (m, 2H), 6.80 (dd, J=8.4, 1.1 Hz, 1H), 6.65-6.45 (m, 3H). Expected: 350 (MH+); Found: 350.

Compound 9: Compound 4-((5-chloropyrimidin-2-yl) oxy)-3-methylaniline xxiv was prepared using 2,5-dichloropyrimidine and 4-amino-2-methylphenol according to the procedure described for the synthesis of compound v. $^1$H NMR (400 MHz, Chloroform-d) δ 8.46 (s, 2H), 6.87 (d, J=8.4 Hz, 1H), 6.60-6.49 (m, 2H), 3.66 (s, 1H), 2.08 (s, 3H).

Compound N-((4-((5-chloropyrimidin-2yl)oxy)-3-methylphenyl)carbamoyl)-2-nitrobenzamide xxv was prepared from 2-nitrobenzoyl isocyanate and 4-((5-chloropyrim-idin-2-yl)oxy)-3-methylaniline according to the procedure described for the synthesis of compound vi. $^1$H NMR (400 MHz, DMSO-d6) δ 11.29 (s, 1H), 10.22 (s, 1H), 8.80 (s, 2H), 8.22 (ddd, J=8.1, 1.2, 0.6 Hz, 1H), 7.94-7.88 (m, 1H), 7.83-7.76 (m, 2H), 7.47 (d, J=19.8 Hz, 2H), 7.13 (d, J=8.6 Hz, 1H), 2.08 (s, 3H).

Compound 2-amino-N-((4-((5-chloropyrimidin-2-yl) oxy)-3-methylphenyl)-carbamoyl)benzamide 9 was prepared from N-((4-((5-chloropyrimidin-2yl)oxy)-3-methylphenyl)carbamoyl)-2-nitrobenzamide xxv according to the procedure described for the synthesis of compound 1. $^1$H NMR (400 MHz, DMSO-d6) δ 10.77 (s, 1H), 10.57 (s, 1H), 8.75 (s, 2H), 7.72 (dd, J=8.1, 1.5 Hz, 1H), 7.53-7.45 (m, 2H), 7.26 (dt, J=8.4, 1.5 Hz, 1H), 7.16-7.08 (m, 1H), 6.79 (dd, J=8.4, 1.2 Hz, 1H), 6.66-6.50 (m, 3H), 2.09 (s, 3H). Expected: 398 (MH+); Found: 398.

Compound 11: Compound 4-((5-methoxypyrimidin-2-yl) oxy)-3-methylaniline xxvii was prepared from 2-chloro-5-methoxypyrimidine and 4-amino-2-methylphenol according to the procedure described for the synthesis of compound v. $^1$H NMR (400 MHz, Chloroform-d) δ 8.20 (s, 2H), 6.87 (d, J=8.4 Hz, 1H), 6.60-6.50 (m, 2H), 3.85 (s, 3H), 2.08 (q, J=0.5 Hz, 3H).

Compound N-((4-((5-methoxypyrimidin-2-yl)oxy)-3-methylphenyl)-carbamoyl)-2-nitrobenzamide xxviii was prepared from 2-nitrobenzoyl isocyanate and 4-((5-methoxypyrimidin-2-yl)oxy)-3-methylaniline according to the procedure described for the synthesis of compound vi. $^1$H NMR (400 MHz, DMSO-d6) δ 11.29 (s, 1H), 10.20 (s, 1H), 8.38 (s, 2H), 8.23-8.18 (m, 1H), 7.94-7.86 (m, 1H), 7.80 (td, J=7.8, 1.2 Hz, 2H), 7.50-7.39 (m, 2H), 7.06 (d, J=8.6 Hz, 1H), 3.86 (s, 3H), 2.07 (s, 3H).

Compound 2-amino-N-((4-((5-methoxypyrimidin-2-yl) oxy)-3-methyl-phenyl)carbamoyl)benzamide 11 was prepared from N-((4-((5-methoxypyrimidin-2-yl)oxy)-3-methylphenyl)carbamoyl)-2-nitrobenzamide according to the procedure described for the synthesis of compound 1. $^1$H NMR (400 MHz, DMSO-d6) δ 10.75 (s, 1H), 10.56 (s, 1H), 8.39 (s, 2H), 7.72 (dd, J=8.1, 1.5 Hz, 1H), 7.50-7.44 (m, 2H), 7.26 (dt, J=8.5, 1.5 Hz, 1H), 7.09-7.03 (m, 1H), 6.79 (dd, J=8.4, 1.2 Hz, 1H), 6.63-6.50 (m, 3H), 3.86 (s, 3H), 2.08 (s, 3H). Expected: 394 (MH+); Found: 394.

Compound 12: Compound N-((4-((5-bromopyrimidin-2-yl)oxy)-3-methyl-phenyl)carbamoyl)benzamide12was prepared from benzoyl isocyanate and 4-((5-bromopyrimidin-2-yl)oxy)-3-methylaniline according to the procedure described for the synthesis of compound vi. $^1$H NMR (400 MHz, DMSO-d6) δ 11.05 (s, 1H), 10.83 (s, 1H), 8.80 (s, 2H), 8.07-8.02 (dd, J=7.4, 1.2 Hz, 2H), 7.66 (t, J=7.4 Hz, 1H), 7.59-7.48 (m, 4H), 7.14 (d, J=8.3 Hz, 1H), 2.09 (s, 3H). Expected: 427 (MH+); Found: 427.

Compound 13: Compound 4-(trifluoromethyl)benzoyl isocyanatexxix was preparedusing 4-(trifluoromethyl)benz-amide and oxalyl chloride in situ according to the procedure described for the synthesis of compound ii.

Compound N-((4-((5-bromopyrimidin-2-yl)oxy)-3-methylphenyl)carbamoyl)-4-(trifluoromethyl)benzamide 13 wasprepared from 4-(trifluoromethyl)benzoyl isocyanate and 4-((5-bromopyrimidin-2-yl)oxy)-3-methylaniline according to the procedure described for the synthesis of compound vi. $^1$H NMR (400 MHz, DMSO-d6) δ 11.28 (s, 1H), 10.68 (s, 1H), 8.80 (s, 2H), 8.20 (d, J=9.6 Hz, 2H), 7.92 (d, J=9.6 Hz, 2H), 7.55-7.47 (m, 2H), 7.14 (d, J=8.5 Hz, 1H), 2.10 (s, 3H). Expected: 495, (MH+); Found: 495.

Compound 14: Compound 4-fluorobenzoyl isocyanatexxx was prepared from 4-fluorobenzamide and oxalyl chloride in situ according to the procedure described for the synthesis of compound ii.

Compound N-((4-((5-bromopyrimidin-2-yl)oxy)-3-methylphenyl)carbamoyl)-4-fluorobenzamide14 wasprepared from 4-fluorobenzoyl isocyanate and 4-((5-bromopyrimidin-2-yl)oxy)-3-methylaniline according to the procedure described for the synthesis of compound vi. $^1$H NMR (400 MHz, DMSO-d6) δ 11.08 (s, 1H), 10.78 (s, 1H), 8.80 (s, 2H), 8.13 (dd, J=8.8, 5.5 Hz, 2H), 7.50 (d, J=8.8 Hz, 2H), 7.39 (t, J=8.8 Hz, 2H), 7.14 (d, J=8.3 Hz, 1H), 2.09 (s, 3H). Expected: 445, (MH+); Found: 445.

Compound 15: Compound 4-methoxybenzoyl isocyanate xxxi was prepared from 4-methoxybenzamide in situ according to the procedure described for the synthesis of compound ii.

Compound N-((4-((5-bromopyrimidin-2-yl)oxy)-3-methylphenyl)carbamoyl)-4-methoxybenzamide15 was prepared from 4-methoxybenzoyl isocyanate and 4-((5-bromopyrimidin-2-yl)oxy)-3-methylaniline according to the procedure described for the synthesis of compound vi. $^1$H NMR (400 MHz, DMSO-d6) δ 10.93 (s, 1H), 10.89 (s, 1H), 8.80 (s, 2H), 8.06 (d, J=8.4 Hz, 2H), 7.50 (d, J=8.0 Hz, 2H), 7.14 (d, J=8.0 Hz, 1H), 7.07 (d, J=4.4 Hz, 2H), 3.86 (s, 3H), 2.09 (s, 3H). Expected: 457, (MH+); Found: 457.

Compound 16: Compound N-((4-(2-morpholinoethoxy) phenyl)carbamoyl)-2-nitrobenzamide xxxii was prepared from 2-nitrobenzoyl isocyanate and 4-(2-morpholinoethoxy)aniline according to the procedure described for the synthesis of compound vi. $^1$H NMR (400 MHz, DMSO-d6) δ 11.23 (s, 1H), 3.71-3.56 (m, 4H), 10.12 (s, 1H), 8.21 (dd, J=8.2, 1.1 Hz, 1H), 7.89 (td, J=7.5, 1.2 Hz, 1H), 7.83-7.70 (m, 2H), 7.46 (d, J=8.5 Hz, 2H), 7.01-6.87 (m, 2H), 4.12 (s, 2H), 2.67 (d, J=82.7 Hz, 8H).

Compound 2-amino-N-((4-(2-morpholinoethoxy)phenyl) carbamoyl)-benzamide 16 was prepared from N-((4-(2-morpholinoethoxy)phenyl)carbamoyl)-2-nitrobenzamide according to the procedure described for the synthesis of compound 1. $^1$H NMR (400 MHz, DMSO-d6) δ 10.61 (s, 1H), 10.50 (s, 1H), 7.71 (dd, J=8.1, 1.5 Hz, 1H), 7.51-7.43 (m, 2H), 7.25 (ddd, J=8.4, 7.0, 1.5 Hz, 1H), 6.98-6.90 (m, 2H), 6.79 (dd, J=8.3, 1.1 Hz, 1H), 6.60-6.50 (m, 3H), 4.07 (t, J=5.8 Hz, 2H), 3.59 (t, J=4.0 Hz, 4H), 2.69 (t, J=5.8 Hz, 2H), 2.48 (t, J=4.0 Hz, 4H). Expected: 385, (MH+); Found: 385.

Compound 17: To a solution of 4-((5-bromopyrimidin-2-yl)oxy)aniline xix (200 mg, 751 µmol) and 1-methyl-4-(4, 4,5,5-tetramethyl-1,3,2-dioxaborolan-2-yl)-1H-pyrazole xxxiii (234.5 mg, 531.5 mmol) in dioxane:H$_2$O(5:1, 3 mL), Na$_2$CO$_3$ (239.0 mg, 2.25 mmol) and Pd(dppf)$_2$Cl$_2$ (61.2 mg, 75.2 µmol) were added sequentially. The mixture was heated in microwave at 100° C. for 1 h. After completion as seen by TLC, the mixture was poured into 20 mL water, and extracted with DCM (3×100 mL). The organic layer was combined, washed with 100 mL water, dried over anhydrous sodium sulfate. Organic solvent was concentrated and the residue was purified using column chromatography to give 220 mg product 4-((5-(1-methyl-1H-pyrazol-4-yl)pyrimidin-2-yl)oxy)aniline xxxiv as yellow solid. $^1$H NMR (400 MHz, Chloroform-d) δ 8.62 (s, 2H), 7.67 (s, 1H), 7.62 (s, 1H), 7.02 (d, J=8.7 Hz, 2H), 6.74 (d, J=8.7 Hz, 2H), 3.98 (s, 3H), 3.75 (s, 2H).

Compound N-((4-((5-(1-methyl-1H-pyrazol-4-yl)pyrimidin-2-yl)oxy)phenyl)-carbamoyl)-2-nitrobenzamide xxxv was prepared from 2-nitrobenzoyl isocynate and 4-((5-(1-methyl-1H-pyrazol-4-yl)pyrimidin-2-yl)oxy)aniline according to the procedure described for the synthesis of compound vi. $^1$H NMR (400 MHz, DMSO-d6) δ 11.30 (s, 1H), 10.26 (s, 1H), 8.86 (s, 2H), 8.27-8.19 (m, 2H), 7.96 (d, J=0.8 Hz, 1H), 7.94-7.86 (m, 1H), 7.80 (ddd, J=8.1, 6.6, 1.6 Hz, 2H), 7.62 (d, J=8.5 Hz, 2H), 7.23-7.17 (m, 2H), 3.89 (s, 3H).

Compound 2-amino-N-((4-((5-(1-methyl-1H-pyrazol-4-yl)pyrimidin-2-yl)oxy)phenyl)carbamoyl)benzamide 17 was prepared from N4(44(5-(1-methyl-1H-pyrazol-4-yl)pyrimidin-2-yl)oxy)phenyl)carbamoyl)-2-nitrobenzamide according to the procedure described for the synthesis of compound 1. $^1$H NMR (400 MHz, DMSO-d6) δ 10.78 (s, 1H), 10.58 (s, 1H), 8.86 (s, 2H), 8.23 (s, 1H), 7.96 (s, 1H), 7.73 (d, J=8.1 Hz, 1H), 7.64 (d, J=9.0 Hz, 2H), 7.26 (ddd, J=8.5, 7.0, 1.5 Hz, 1H), 7.21 (d, J=9.0 Hz, 2H), 6.80 (d, J=8.4 Hz, 1H), 6.63-6.52 (m, 3H), 3.89 (s, 3H). Expected: 430, (MH+); Found: 430.

Compound 18: Compound 4-methoxybenzoyl isocyanate xxxi was prepared from 4-methoxybenzamide in situ according to the procedure described for the synthesis of compound ii.

Compound N-((4-((5-bromopyrimidin-2-yl)oxy)phenyl)carbamoyl)-4-methoxybenzamide 18 was prepared from 4-methoxybenzoyl isocyanate and 4-((5-bromopyrimidin-2-yl)oxy)aniline according to the procedure described for the synthesis of compound vi. $^1$H NMR (400 MHz, DMSO-d6) δ 10.95 (s, 1H), 10.90 (s, 1H), 8.81 (s, 2H), 8.07 (d, J=9.0 Hz, 2H), 7.65 (d, J=9.1 Hz, 2H), 7.22 (d, J=8.9 Hz, 2H), 7.08 (d, J=9.0 Hz, 2H), 3.87 (s, 3H). Expected: 443, (MH+) Found: 465.01 (M+Na+).

Compound 19: Compound 3-chloro-4-((5-chloropyrimidin-2-yl)oxy)aniline xxxvii was prepared from 2,5-dichloropyrimidine and 4-amino-2-chlorophenol according to the procedure described for the synthesis of compound v. $^1$H NMR (400 MHz, Chloroform-d) δ 8.50 (s, 2H), 7.04 (dd, J=8.6, 0.2 Hz, 1H), 6.80 (dd, J=2.7, 0.2 Hz, 1H), 6.63 (dd, J=8.6, 2.7 Hz, 1H), 3.77 (s, 2H).

Compound N-((3-chloro-4-((5-chloropyrimidin-2-yl)oxy)phenyl)carbamoyl)-4-methoxybenzamide 19 prepared from 3-chloro-4-((5-chloropyrimidin-2-yl)oxy)anilineand 4-methoxybenzoyl isocyanate according to the procedure described for the synthesis of compound vi. $^1$H NMR (400 MHz, DMSO-d6) δ 11.21 (s, 1H), 9.68 (s, 1H), 8.41 (d, J=6.1 Hz, 1H), 7.92-7.86 (m, 2H), 7.48 (d, J=8.7 Hz, 1H), 7.21 (dd, J=8.7, 2.5 Hz, 1H), 4.92 (s, 2H), 3.23 (d, J=0.8 Hz, 3H), 3.10 (s, 3H), 2.90 (s, 3H), 2.76 (d, J=0.7 Hz, 3H). Expected: 433, (MH+); Found: 433.

Compound 20: Compound 3-methyl-4-((5-(1-methyl-1H-pyrazol-4-yl)pyrimidin-2-yl)oxy)aniline xxxviii was prepared from 4-((5-bromopyrimidin-2-yl)oxy)-3-methylaniline and 1-methyl-4-(4,4,5,5-tetramethyl-1,3,2-dioxaborolan-2-yl)-1H-pyrazole according to the procedure described for the synthesis of compound xxxiv. $^1$H NMR (400 MHz, Chloroform-d) δ 8.61 (s, 2H), 7.71 (d, J=0.8 Hz, 1H), 7.66-7.59 (m, 1H), 6.92 (d, J=8.4 Hz, 1H), 6.66-6.51 (m, 2H), 3.97 (s, 3H), 3.58-3.15 (m, 2H), 2.12 (s, 3H).

Compound 4-methoxy-N-((44(5-(1-methyl)-1H-pyrazol-4-yl)pyrimidin-2-yl)oxy)phenyl)carbamoyl)benzamide 20 was prepared from 4-methoxybenzoyl isocyanate and 3-methyl-4-((5-(1-methyl-1H-pyrazol-4-yl)pyrimidin-2-yl)oxy)aniline according to the procedure described for the synthesis of compound vi. $^1$H NMR (400 MHz, DMSO-d6) δ 10.94 (s, 1H), 10.88 (s, 1H), 8.84 (s, 2H), 8.22 (s, 1H), 8.07 (d, J=9.0 Hz, 2H), 7.94 (d, J=0.8 Hz, 1H), 7.51 (d, J=0.8 Hz, 2H), 7.12 (m, 1H), 7.08 (d, J=9.0 Hz, 2H), 3.89 (s, 3H), 3.86 (s, 3H), 2.11 (s, 3H). Expected: 458, (MH+); Found: 458.

Compound 21: Compound 4-((5-bromopyrimidin-2-yl)oxy)-N-methylaniline xl was prepared from 5-bromo-2-chloropyrimidine and 4-(methylamino)phenol according to the procedure described for the synthesis of compound v. $^1$H NMR (400 MHz, Chloroform-d) δ 8.35 (s, 2H), 7.08 (d, J=8.8 Hz, 2H), 6.74 (d, J=8.8 Hz, 2H), 6.52 (s, 1H), 3.47 (s, 3H).

Compound N-((4-((5-bromopyrimidin-2-yl)oxy)phenyl)(methyl)carbamoyl)-4-methoxybenzamide 21 was prepared from 4-methoxybenzoyl isocyanate and 4-((5-bromopyrimidin-2-yl)oxy)-N-methylaniline according to the procedure described for the synthesis of compound vi. $^1$H NMR (400 MHz, Chloroform-d) δ 8.38 (s, 1H), 8.35 (s, 2H), 7.90 (d, J=8.9 Hz, 2H), 7.35 (d, J=9.0 Hz, 2H), 7.28 (d, J=3.2 Hz, 2H), 7.01 (d, J=8.9 Hz, 2H), 3.91 (s, 3H), 3.52 (s, 3H). Expected: 457, (MH+); Found: 457.

Compound 22: Compound picolinoyl isocyanate xli was prepared in situ from picolinamide according to the procedure described for the synthesis of compound ii.

Compound N-((4-((5-bromopyrimidin-2-yl)oxy)-3-methylphenyl)carbamoyl)-picolinamide 22 prepared from picolinoyl isocyanate and 4-((5-bromopyrimidin-2-yl)oxy)-3-methylaniline according to the procedure described for the synthesis of compound vi. $^1$H NMR (400 MHz, Chloroform-d) δ 10.59 (s, 1H), 10.11 (s, 1H), 8.69 (dd, J=4.7, 1.7 Hz, 1H), 8.58 (s, 2H), 8.28 (dd, J=7.8, 1.1 Hz, 1H), 7.98 (td, J=7.7, 1.7 Hz, 1H), 7.62-7.57 (m, 2H), 7.52 (dd, J=8.0, 4.0 Hz, 1H), 7.10 (d, J=8.6 Hz, 1H), 2.22 (s, 3H). Expected: 428, (MH+); Found: 428.

Compound 23: Compound N-((3-methyl-4-nitrophenyl)carbamoyl)benzamide xliii was prepared from benzoyl isocyanate and 3-methyl-4-nitroaniline according to the procedure described for the synthesis of compound vi. $^1$H NMR (400 MHz, DMSO-d6) δ 11.21 (s, 1H), 11.14 (s, 1H), 8.12-8.00 (m, 3H), 7.77 (ddd, J=9.0, 2.4, 0.6 Hz, 1H), 7.72-7.63 (m, 2H), 7.61-7.51 (m, 2H), 2.58 (s, 3H).

Compound N-((4-amino-3-methylphenyl)carbamoyl)benzamide xliv was prepared from N-((3-methyl-4-nitrophenyl)carbamoyl)benzamide according to the procedure described for the synthesis of compound 1. $^1$H NMR (400 MHz, DMSO-d6) δ 10.86 (s, 1H), 10.48 (s, 1H), 8.06-7.97 (m, 2H), 7.68-7.60 (m, 1H), 7.58-7.48 (m, 2H), 7.15-7.06 (m, 2H), 6.60 (d, J=8.2 Hz, 1H), 4.76 (s, 2H), 2.08 (s, 3H).

To a solution of N-((4-amino-3-methylphenyl)carbamoyl)benzamide xliv (100 mg, 0.37 mmol) in anhydrous DMF (15 mL) was added 1,3-bis(t-butylcarbonyl)-2-methylthiopseudourea xlv (161 mg, 0.55 mmol), triethylamine (169 mg, 1.67 mmol), and mercury(II) chloride (151 mg, 0.55 mmol). The suspension was kept stirring at room temperature for overnight. The reaction mixture was diluted with DCM, washed with Na$_2$CO$_3$ solution. The organic layer was washed with water and brine, dried over Na$_2$SO$_4$, and then concentrated under vacuum. The residue was treated with 0.5 mL TFA in 5 mL DCM. The mixture was stirred overnight and basified with ammonium hydroxide to pH=9. The mixture was extracted with DCM (3×30 mL) and the solvent was evaporated. The product N-((4-guanidino -3-methylphenyl)carbamoyl)benzamide 23 was purified using column chromatography to afford 40 mg product 23. $^1$H NMR (400 MHz, DMSO-d6) δ 11.08 (s, 1H), 10.90 (s, 1H), 9.54 (s, 1H), 8.05 (dd, J=1.9, 0.9 Hz, 1H), 8.03 (t, J=1.0 Hz, 1H), 7.66 (d, J=7.5 Hz, 1H), 7.60-7.53 (m, 4H), 7.40 (s, 3H), 7.21 (d, J=9.3 Hz, 1H), 2.23 (s, 3H). Expected: 312, (MH+); Found: 312.

Compound 24: A solution of 1-isocyanato-2-nitrobenzene (100 mg, 0.6 mmol) in dry 1,4-dioxane (5 mL) was added dropwise to a solution of 4-((5-bromopyrimidin-2-yl)oxy)-3-methylaniline v (168 mg, 0.6 mmol) in dry DCM (3 mL) with stirring at room temperature. The mixture was stirred for 18 h and then diluted with water. The precipitated solid was collected by filtration and washed with water. The solid was dissolved in ethyl acetate, and the organic layer was washed with water 2-3 times, dried and concentrated to give 190 mg of 1-(4-((5-bromopyrimidin-2-yl)oxy)-3-methylphenyl)-3-(2-nitrophenyl)urea xlvi. $^1$H NMR (400 MHz, DMSO-d$_6$)δ 9.84 (s, 1H), 9.60 (s, 1H), 8.79 (d, J=0.8 Hz, 1H), 8.32 (dt, J=8.6, 1.2 Hz, 1H), 8.11 (dt, J=8.5, 1.2 Hz, 1H), 7.71 (ddd, J=8.6, 7.2, 1.5 Hz, 1H), 7.50-7.39 (m, 1H), 7.35 (ddd, J=8.7, 2.6, 0.7 Hz, 1H), 7.22 (ddt, J=8.5, 7.0, 1.3 Hz, 1H), 7.08 (d, J=8.7 Hz, 1H), 5.76 (d, J=0.8 Hz, 1H), 2.07 (s, 2H).

Iron powder (160 mg, 3.0 mmol) was added in portions to a mixture of 1-(4-((5-bromopyrimidin-2-yl)oxy)-3-methylphenyl)-3-(2-nitrophenyl)urea (221 mg, 0.5 mmol) and NH$_4$Cl (335 mg, 6 mmol) in EtOH (20 mL) at 80° C. The reaction mixture was refluxed for 30 min and then cooled to room temperature and diluted with water. The precipitated solid was collected by filtration. The solid was dissolved in an excess of ethyl acetate and filtered. Ethyl acetate was evaporated to give a residue which was then purified using column chromatography (ethyl acetate:hexanes 2:3) to obtain 85 mg of 1-(2-aminophenyl)-3-(4-((5-bromopyrimidin-2-yl)oxy)-3-methylphenyl)urea 24. $^1$H NMR (400 MHz, DMSO-d6) δ 8.79 (s, 2H), 8.74 (s, 1H), 7.74 (s, 1H), 7.41-7.38 (m, 1H), 7.36 (dd, J=7.9, 1.5 Hz, 1H), 7.30 (dt, J=8.7, 0.6 Hz, 1H), 7.04 (d, J=8.7 Hz,1H), 6.85 (ddd, J=7.8, 7.2, 1.5 Hz, 1H), 4.79 (s, 2H), 2.05 (s, 3H). MS Expected: 414.05, (MH+); Found: 414.05.

Compound 25: Compound N-((4-((5-chloropyrimidin-2-yl)oxy)-3-methylphenyl)carbamoyl)-4-(trifluoromethyl) benzamide 25 was prepared from 4-(trifluoromethyl)benzoyl isocyanate and 4-((5-chloropyrimidin-2-yl)oxy)-3-methylaniline according to the procedure described for the synthesis of compound vi. $^1$H NMR (400 MHz, DMSO-d6) δ 11.28 (s, 1H), 10.68 (s, 1H), 8.75 (s, 2H), 8.20 (d, J=8.0 Hz, 2H), 7.91 (d, J=8.4 Hz, 2H), 7.56-7.47 (m, 2H), 7.14 (d, J=8.4 Hz, 1H), 2.10 (s, 3H). MS Expected: 451, Found: 451.07

Compound 26: Compound N-((4-((5-methoxypyrimidin-2-yl)oxy)-3-methylphenyl)carbamoyl)-4-(trifluoromethyl) benzamide 26 was prepared from 4-(trifluoromethyl)benzoyl isocyanate and 4-((5-methoxypyrimidin-2-yl)oxy)-3-methylaniline according to the procedure described for the synthesis of compound vi. $^1$H NMR (400 MHz, DMSO-d6) δ 11.27 (s, 1H), 10.66 (s, 1H), 8.39 (s, 2H), 8.20 (d, J=8.0 Hz, 2H), 7.93 (d, J=8.4 Hz, 2H), 7.53-7.44 (m, 2H), 7.08 (d, J=8.5 Hz, 1H), 3.86 (s, 3H), 2.09 (s, 3H). MS Expected: 447, Found: 447

Compound 27: Compound 4-((5-chloropyrimidin-2-yl) oxy)-3-fluoroaniline xlvii was synthesized from 4-amino-2-fluorophenol and 2,5-dichloropyrimidine using procedure similar to compound v. $^1$H NMR (400 MHz, Chloroform-d) δ 8.49 (s, 2H), 7.02 (dd, J=8.6, 0.4 Hz, 1H), 6.55-6.44 (m, 2H), 3.78 (s, 2H). MS Expected: 240, Found: 240

Compound N4(44(5-chloropyrimidin-2-yl)oxy)-3-fluorophenyl)carbamoyl)-4-(trifluoromethyl)benzamide 27 was prepared from 4-((5-chloropyrimidin-2-yl)oxy)-3-fluoroaniline and 4-(trifluoromethyl)benzoyl isocyanate according to the procedure described for the synthesis of compound vi. $^1$H NMR (400 MHz, DMSO-d6) δ 11.36 (s, 1H), 10.78 (s, 1H), 8.80 (s, 2H), 8.20 (d, J=8.4 Hz, 2H), 7.94 (d, J=8.4 Hz, 2H), 7.79 (dd, J=12.0, 4.0 Hz, 2H), 7.47-7.35 (m, 2H). MS Expected: 455, Found: 455

Compound 28: Compound N-((3-methyl-4-(pyrazin-2-yloxy)phenyl)-carbamoyl)-4-(trifluoromethyl)benzamide 28 was prepared from 3-methyl-4-(pyrazin-2-yloxy)aniline and 4-(trifluoromethyl)benzoyl isocyanate according to the procedure described for the synthesis of compound vi. $^1$H NMR (400 MHz, DMSO-d6) δ 11.29 (s, 1H), 10.68 (s, 1H), 8.58-8.53 (m, 1H), 8.36 (d, J=2.7 Hz, 1H), 8.24-8.15 (m, 3H), 7.93 (d, J=8.4 Hz, 2H), 7.57-7.47 (m, 2H), 7.13 (d, J=8.6 Hz, 1H), 2.11 (s, 3H). MS Expected: 417, Found: 417

Compound 29: Compound N-((4-((2-chloropyrimidin-5-yl)oxy)-3-methylphenyl)carbamoyl)-4-(trifluoromethyl) benzamide 29 was prepared from 4-((2-chloropyrimidin-5-yl)oxy)-3-methylaniline and 4-(trifluoromethyl)benzoyl isocyanate according to the procedure described for the synthesis of compound vi. $^1$H NMR (400 MHz, DMSO-d6) δ 11.29 (s, 1H), 10.70 (s, 1H), 8.50 (s, 2H), 8.20 (d, J=8.1 Hz, 2H), 7.91 (d, J=8.1 Hz, 2H), 7.60 (d, J=2. Hz, 1H), 7.13 (d, J=8.6 Hz, 1H), 2.23 (s, 3H). MS Expected: 451, Found: 451

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A compound selected from the group consisting of:

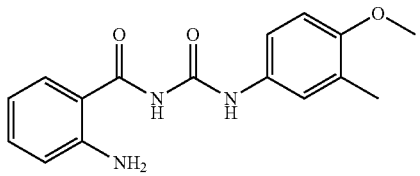 [SMILES: COc1ccc(NC(=O)NC(=O)c2ccccc2N)cc1C]

2-amino-N-((4-methoxy-3-methylphenyl)carbamoyl) benzamide,

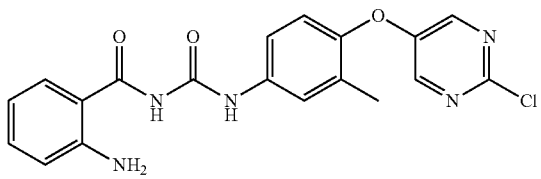 [SMILES: Cc1cc(NC(=O)NC(=O)c2ccccc2N)ccc1Oc1cnc(Cl)nc1]

2-amino-N-((4-((2-chloropyrimidin-5-yl)oxy)-3-methylphenyl)-carbamoyl)benzamide,

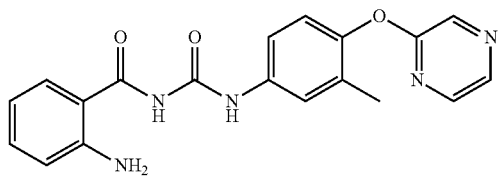 [SMILES: Cc1cc(NC(=O)NC(=O)c2ccccc2N)ccc1Oc1cnccn1]

2-amino-N-((3-methyl-4-(pyrazine-2-yloxy)phenyl)carbamoyl)-benzamide,

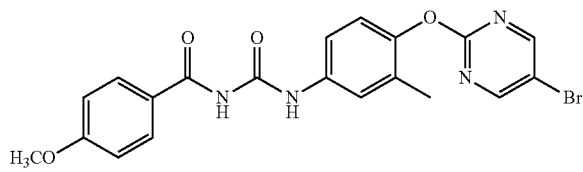

N-((4-((5-bromopyrimidin-2-yl)oxy)-3-methylphenyl)carbamoyl)-4-methoxybenzamide,

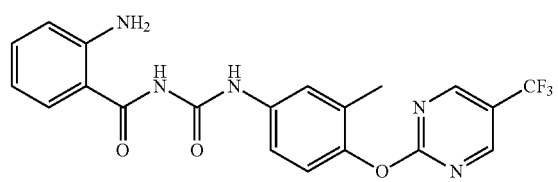 [SMILES: Cc1cc(NC(=O)NC(=O)c2ccccc2N)ccc1Oc1ncc(C(F)(F)F)cn1]

2-amino-N-((3-methyl-4-((5-(trifluoromethyl)pyrimidin-2-yl)oxy)phenyl)carbamoyl)benzamide,

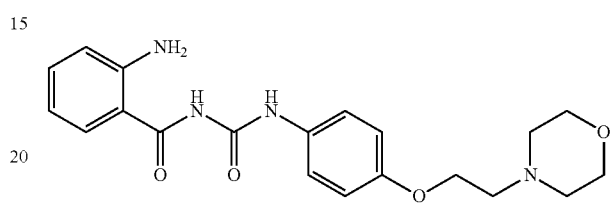

2-amino-N-((4-(2-morpholinoethoxy)phenyl)carbamoyl)benzamide,

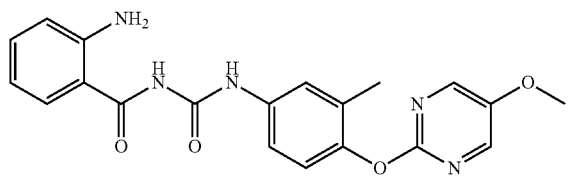 [SMILES: COc1cnc(Oc2ccc(NC(=O)NC(=O)c3ccccc3N)cc2C)nc1]

2-amino-N-((4-((5-methoxypyrimidin-2-yl)oxy)-3-methylphenyl)carbamoyl)benzamide,

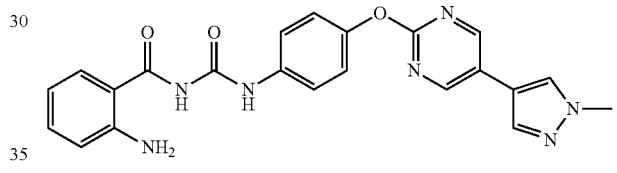

2-amino-N-((4-((5-(1-methyl-1H-pyrazol-4-yl)pyrimidin-2-yl)oxy)phenyl)carbamoyl)benzamide,

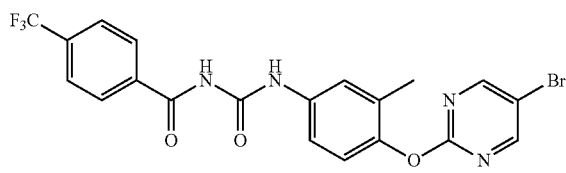 [SMILES: Cc1cc(NC(=O)NC(=O)c2ccc(C(F)(F)F)cc2)ccc1Oc1ncc(Br)cn1]

N-((4-((5-bromopyrimidin-2-yl)oxy)-3-methylphenyl)carbamoyl)-4-(trifluoromethyl)benzamide,

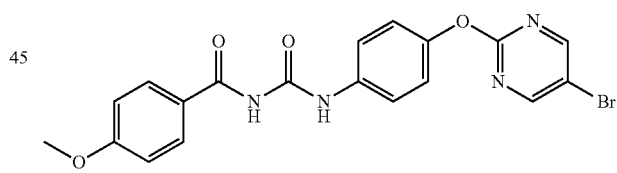

N-((4-((5-bromopyrimidin-2-yl)oxy)phenyl)carbamoyl)-4-methoxybenzamide,

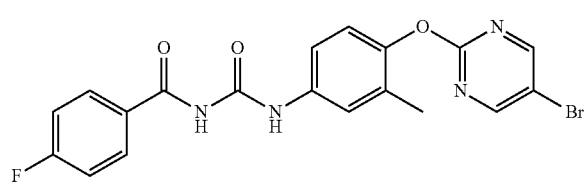 [SMILES: Cc1cc(NC(=O)NC(=O)c2ccc(F)cc2)ccc1Oc1ncc(Br)cn1]

N-((4-((5-bromopyrimidin-2-yl)oxy)-3-methylphenyl)carbamoyl)-4-fluorobenzamide,

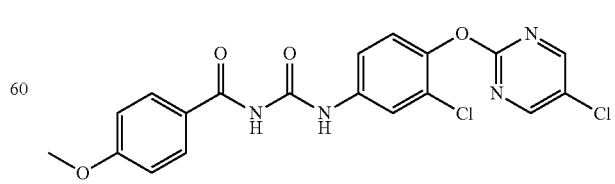

N-((3-chloro-4-((5-chloropyrimidin-2-yl)oxy)phenyl)carbamoyl)-4-methoxybenzamide,

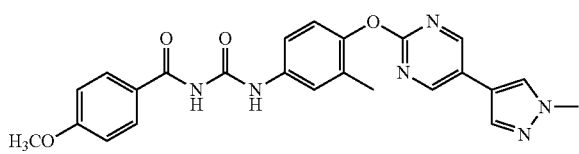 [SMILES: COc1ccc(C(=O)NC(=O)Nc2ccc(Oc3ncc(-c4cnn(C)c4)cn3)c(C)c2)cc1]

4-methoxy-N-((3-methyl-4-((5-(1-methyl-1H-pyrazol-4-yl)pyrimidin-2-yl)oxy)phenyl)carbamoyl)benzamide,

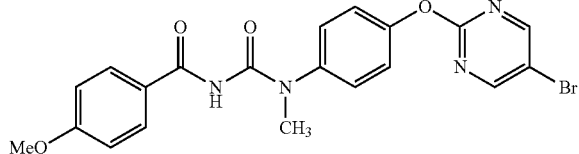 [SMILES: COc1ccc(C(=O)NC(=O)N(C)c2ccc(Oc3ncc(Br)cn3)cc2)cc1]

N-((4-((5-bromopyrimidin-2-yl)oxy)phenyl)(methyl)carbamoyl)-4-methoxybenzamide,

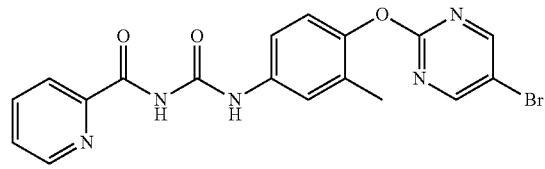 [SMILES: Cc1cc(NC(=O)NC(=O)c2ccccn2)ccc1Oc1ncc(Br)cn1]

N-((4-((5-bromopyrimidin-2-yl)oxy)-3-methylphenyl)carbamoyl)picolinamide,

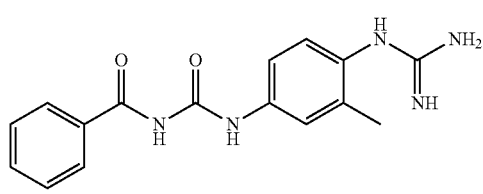 [SMILES: Cc1cc(NC(=O)NC(=O)c2ccccc2)ccc1NC(=N)N]

N-((4-guanidino-3-methylphenyl)carbamoyl)benzamide,

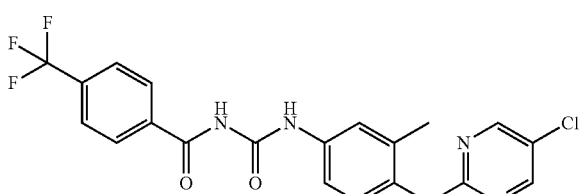

N-((4((5-chloropyrimidin-2-yl)oxy)-3-methylphenyl)carbamoyl)-4-(trifluoromethyl)benzamide,

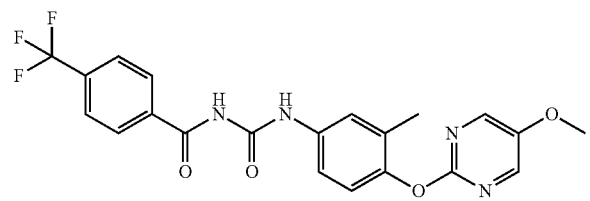 [SMILES: COc1cnc(Oc2ccc(NC(=O)NC(=O)c3ccc(C(F)(F)F)cc3)cc2C)nc1]

N-((4((5-methoxypyrimidin-2-yl)oxy)-3-methylphenyl)carbamoyl)-4-(trifluoromethyl)benzamide,

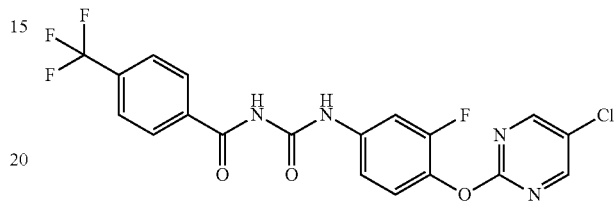

N-((4-((5-chloropyrimidin-2-yl)oxy)-3-fluorophenyl)carbamoyl)-4-(trifluoromethyl)benzamide,

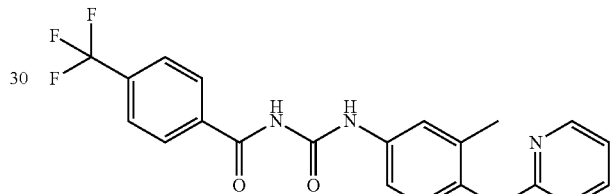

N-((3-methyl-4-(pyrazin-2-yloxy)phenyl)-carbamoyl)-4-(trifluoromethyl)benzamide, and

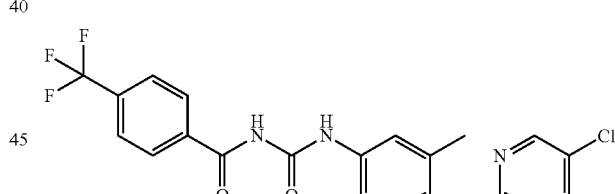

N-((4-((2-chloropyrimidin-5-yl)oxy)-3-methylphenyl)carbamoyl)-4-(trifluoromethyl)benzamide, including a pharmaceutically acceptable salt thereof, or a prodrug thereof, or a mixture thereof.

2. A pharmaceutical composition comprising a compound of claim 1.

3. A method of treating a clinical condition associated with hTERT overexpression comprising administering to a subject suffering from the clinical condition associated with hTERT overexpression a therapeutically effective amount of the pharmaceutical composition of claim 2.

4. The method of claim 3, wherein the clinical condition associated with hTERT overexpression is due to copy number changes, translocations, missense mutations, and epigenetic changes or other genetic mechanisms.

5. The method of claim 3, wherein said clinical condition associated with hTERT overexpression is cancer.

6. The method of claim 5, wherein the cancer is selected from one or more of glioblastoma, bladder cancer, melanoma, thyroid, liver cancer, kidney cancer, stomach, esophagus cancer, lung cancer or neuroblastoma.

7. A kit comprising a compound of claim 1 and instructions for administering said compound to a subject suffering from a clinical condition associated with hTERT overexpression.

8. The kit of claim 7, wherein the clinical condition associated with hTERT overexpression is cancer.

9. The kit of claim 8, wherein the cancer is selected from one or more of glioblastoma, bladder cancer, melanoma, thyroid, liver cancer, kidney cancer, stomach, esophagus cancer, lung cancer or neuroblastoma.

10. The kit of claim 7, further comprising one or more anticancer agents.

11. The kit of claim 10, wherein said compound is to be administered together with one or more anticancer agents.

* * * * *

UNITED STATES PATENT AND TRADEMARK OFFICE
CERTIFICATE OF CORRECTION

PATENT NO. : 10,556,860 B2
APPLICATION NO. : 15/779132
DATED : February 11, 2020
INVENTOR(S) : Hurley et al.

It is certified that error appears in the above-identified patent and that said Letters Patent is hereby corrected as shown below:

On the Title Page

Item (73), the Assignee should read:
Assignee: ARIZONA BOARD OF REGENTS ON BEHALF OF THE UNIVERSITY OF ARIZONA, Tucson, AZ (US)

Signed and Sealed this
Twenty-fifth Day of October, 2022

Katherine Kelly Vidal
*Director of the United States Patent and Trademark Office*